(12) United States Patent
Moehring et al.

(10) Patent No.: US 8,162,837 B2
(45) Date of Patent: Apr. 24, 2012

(54) MEDICAL DOPPLER ULTRASOUND SYSTEM FOR LOCATING AND TRACKING BLOOD FLOW

(75) Inventors: Mark A. Moehring, Seattle, WA (US); Mark A. Curry, Lynnwood, WA (US)

(73) Assignee: Spentech, Inc., Seattle, WA (US)

( * ) Notice: Subject to any disclaimer, the term of this patent is extended or adjusted under 35 U.S.C. 154(b) by 1316 days.

(21) Appl. No.: 11/152,666

(22) Filed: Jun. 13, 2005

(65) Prior Publication Data

US 2007/0016050 A1    Jan. 18, 2007

(51) Int. Cl.
*A61B 8/00* (2006.01)

(52) U.S. Cl. ......... 600/454; 600/437; 600/453; 600/455

(58) Field of Classification Search ........... 600/437–463
See application file for complete search history.

(56) References Cited

U.S. PATENT DOCUMENTS

| | | | |
|---|---|---|---|
| 4,014,206 A | 3/1977 | Taylor | 73/19 |
| 4,015,464 A | 4/1977 | Miller et al. | 73/61 R |
| 4,152,928 A | 5/1979 | Roberts | 73/61 R |
| 4,276,491 A | 6/1981 | Daniel | 310/317 |
| 4,319,580 A | 3/1982 | Colley et al. | 128/661 |
| 4,501,277 A | 2/1985 | Hongo | 128/660 |
| 4,537,074 A | 8/1985 | Dietz | 73/625 |
| 4,751,929 A | 6/1988 | Hayakawa et al. | 128/663 |
| 4,800,891 A | 1/1989 | Kim | 128/661.09 |
| 4,848,354 A | 7/1989 | Angelsen et al. | 128/660.05 |
| 4,896,674 A | 1/1990 | Seo | 128/661.09 |
| 4,932,415 A | 6/1990 | Angelsen et al. | 128/661.09 |
| 4,993,417 A | 2/1991 | Seo | 128/661.09 |
| 5,053,008 A | 10/1991 | Bajaj | 604/104 |
| 5,083,567 A | 1/1992 | Uchibori | 128/661.09 |
| 5,101,828 A | 4/1992 | Welkowitz et al. | 128/668 |
| 5,103,826 A | 4/1992 | Bonnefous | 128/661.08 |
| 5,103,827 A | 4/1992 | Smith | 128/661.08 |
| 5,129,399 A | 7/1992 | Hirama | 128/661.01 |

(Continued)

FOREIGN PATENT DOCUMENTS

AU    765304    1/2004

(Continued)

OTHER PUBLICATIONS

Zagzebski, James A., "Essentials of Ultrasound Physics", Mosby, Inc., St. Louis, Missouri, 1996. pp. 46-48 and 109-122.

(Continued)

*Primary Examiner* — Brian Casler
*Assistant Examiner* — Amanda Lauritzen
(74) *Attorney, Agent, or Firm* — Dorsey & Whitney LLP

(57) ABSTRACT

Systems and methods for processing echo signals in a Doppler ultrasound system from a region of interest. An ultrasound beam is electronically steered to deliver ultrasound to and receive echo signals from a plurality of sample locations in the region of interest. The echo signals for each sample location are processed to extract Doppler shift signals and Doppler shift data representing the Doppler shift signals are generated. The Doppler shift data accumulated for the sample locations can be used to detect the presence of blood flow in the region of interest, and identify the location in the region of interest at which the presence of blood flow is detected. The blood flow can be tracked by updating the location of the detected blood flow in the region of interest. The blood flow can be further monitored by combining the locating and tracking functionality with an m-mode ultrasound image.

13 Claims, 14 Drawing Sheets

U.S. PATENT DOCUMENTS

| | | | |
|---|---|---|---|
| 5,148,808 A | 9/1992 | Satake | 128/660.05 |
| 5,190,044 A | 3/1993 | Kawasaki et al. | 128/661.09 |
| 5,231,573 A | 7/1993 | Takamizawa | 364/413.25 |
| 5,249,577 A | 10/1993 | Shinomura et al. | 128/660.05 |
| 5,271,404 A | 12/1993 | Corl et al. | 128/661.08 |
| 5,348,015 A | 9/1994 | Moehring et al. | 128/661.07 |
| 5,441,051 A | 8/1995 | Hileman et al. | 128/661.08 |
| 5,476,097 A | 12/1995 | Robinson | 128/660.05 |
| 5,501,223 A | 3/1996 | Washburn et al. | 128/661.09 |
| 5,513,640 A | 5/1996 | Yamazaki et al. | 128/661.09 |
| RE35,371 E | 11/1996 | Seo | 128/661.09 |
| 5,590,658 A | 1/1997 | Chiang et al. | 128/661.01 |
| 5,615,680 A | 4/1997 | Sano | 128/661.09 |
| 5,622,173 A | 4/1997 | Bisson et al. | 128/661.01 |
| 5,722,412 A | 3/1998 | Pflugrath et al. | 128/662.03 |
| 5,732,705 A | 3/1998 | Yokoyama et al. | 128/660.07 |
| 5,785,654 A | 7/1998 | Iinuma et al. | 600/441 |
| 5,785,655 A | 7/1998 | Goodsell, Jr. et al. | 600/441 |
| 5,800,356 A | 9/1998 | Criton et al. | 600/441 |
| 5,833,615 A | 11/1998 | Wu et al. | 600/458 |
| 5,860,927 A | 1/1999 | Sakaguchi et al. | 600/453 |
| 5,882,315 A | 3/1999 | Ji et al. | 600/553 |
| 5,910,118 A | 6/1999 | Kanda et al. | 600/455 |
| 5,913,824 A | 6/1999 | Ogasawara et al. | 600/455 |
| 5,919,139 A | 7/1999 | Lin | 600/443 |
| 5,924,991 A | 7/1999 | Hossack et al. | 600/443 |
| 5,947,904 A | 9/1999 | Hossack et al. | 600/458 |
| 5,997,478 A | 12/1999 | Jackson et al. | 600/437 |
| 6,045,505 A | 4/2000 | Holley et al. | 600/441 |
| 6,196,972 B1 | 3/2001 | Moehring | 600/454 |
| 6,482,161 B1 | 11/2002 | Sumanaweera et al. | 600/454 |
| 6,503,202 B1 | 1/2003 | Hossack et al. | 600/454 |
| 6,524,249 B2 | 2/2003 | Moehring et al. | 600/438 |
| 6,547,732 B2 | 4/2003 | Jago | 600/437 |
| 6,547,736 B1 | 4/2003 | Moehring et al. | 600/454 |
| 6,616,611 B1 | 9/2003 | Moehring | 600/454 |
| 6,635,017 B1 | 10/2003 | Moehring et al. | 600/439 |
| 7,128,713 B2 | 10/2006 | Moehring et al. | 600/453 |
| 7,537,568 B2 | 5/2009 | Moehring | 600/454 |
| 2002/0091319 A1 | 7/2002 | Moehring et al. | 600/454 |
| 2004/0019278 A1 | 1/2004 | Abend | 600/454 |
| 2004/0138563 A1 | 7/2004 | Moehring et al. | 600/439 |
| 2005/0033174 A1 | 2/2005 | Moehring et al. | 600/453 |
| 2005/0075568 A1 | 4/2005 | Moehring | 600/453 |
| 2005/0101863 A1* | 5/2005 | Kawagishi et al. | 600/443 |
| 2005/0251041 A1 | 11/2005 | Moehring | 600/441 |
| 2006/0264759 A1 | 11/2006 | Moehring et al. | 600/469 |

FOREIGN PATENT DOCUMENTS

| | | |
|---|---|---|
| EP | 0 079 453 A1 | 5/1983 |
| EP | 0 164 835 B1 | 1/1989 |
| EP | 1182452 A2 | 2/2002 |
| JP | 2002-52913 | 2/2002 |
| TW | 2005-18718 | 6/2005 |
| TW | 2006-12869 | 5/2006 |
| TW | 2007-01954 | 1/2007 |
| WO | 94/06353 A2 | 3/1994 |
| WO | WO 96/21215 | 7/1996 |
| WO | 00/27288 | 5/2000 |
| WO | 2005/006952 A2 | 1/2005 |
| WO | 2005/112771 A2 | 12/2005 |
| WO | 2006/127542 A2 | 11/2006 |
| WO | 2006/138185 A2 | 12/2006 |
| WO | 2007/022055 A1 | 2/2007 |

OTHER PUBLICATIONS

*Aloka-860 Operational Manual.* vol. I System Description, Effective S/N: 51M8876 and above. pp. i-15-2 and A-2-A-5.

*Aloka Color Doppler Model SSD-860 Cardiovascular Scanner* Sales Brochure. Aloka Co., Ltd., Japan.

Demchuk, A.M. et al., "Thrombolysis in Brain Ischemia (TIBI) Transcranial Doppler Flow Grades Predict Clinical Severity, Early Recovery, and Mortality in Patients Treated with Intravenous Tissue Plasminogen Activator", American Heart Association, Inc., Jan. 2001. pp. 89-93.

Duncan, Walter J. *Color Doppler in Clinical Cardiology.* Philadelphia, W.B. Saunders Company, Harcourt Brace Jovanovich, Inc., 1988. pp. 1-13.

Ferrera, K. et al., "Color Flow Mapping," Ultrasound in Medicine and Biology, vol. 23, No. 3, 1997, pp. 321-345.

Giller, C.A. et al., "Oscillations in Cerebral Blood Flow Detected with a Transcranial Doppler Index", Journal of Cerebral Blood Flow and Metabolism, vol. 19, No. 4, Apr. 1999. pp. 452-459.

Griffith, James M. et al., "An Ultrasound System for Combined Cardiac Imaging and Doppler Blood Flow Measurement in Man", Biomedical Engineering and Instrumentation Branch, Division of Research Services and the Cardiology Branch, National Heart, Lung, and Blood Institute, Maryland, vol. 57, No. 5, May 1978, pp. 925-930.

Iwase, Masatsugu et al. *Clinical Echocardiography.* Dordrecht, Kluwer Academic Publishers, 1989. pp. 11-27 and 250-281.

Kremkau, G.W. *Doppler Ultrasound, Principles and Instruments.* (Philadelphia, W.B. Saunders Company, 1990), pp. 177-211.

Missri, José*Clinical Doppler Echocardiography Spectral and Color Flow Imaging.* New York, McGraw-Hill, Inc., 1990. pp. 9-27 and 279-303.

Omoto, R. et al., "The Development of Real-Time Two-Dimensional Doppler Echocardiography and Its Clinical Significance in Acquired Valvular Diseases With Special Reference to the Evaluation of Valvular Regurgitation", Reprinted from *Japanese Heart Journal,* vol. 25, No. 3, pp. 325-340, May 1984.

Omoto, R. et al., Clinical Significance and Prospects of "Real-Time Two-Dimensional Doppler Echocardiography", Color ATLAS of Real-Time Two-Dimensional Doppler Echocardiography, Chapter 1-6, pp. 1-44, Shindan-To-Chiryo Co., Ltd. Tokyo 1984.

"Operation Manual for Diagnostic Ultrasound Equipment Model SSH-160A (2B730-405E*B)", Toshiba Corporation, 1987, pp. 7-4-7-5, 8-1, 11-1-11-3, 11-12, 12-1, 12-3 and 16-10.

Redel, Dierk A. *Color Blood Flow Imaging of the Heart.* Germany, Springer-Verlag Berlin Heidelberg, 1988. pp. 5-12 and 27-41.

Weyman, Arthur E. *Principles and Practice of Echocardiography,* 2d ed. Philadelphia, Lea & Febiger, 1994. pp. 218-233 and 256-281.

Moehring, M.A. et al., "Power M-Mode Doppler (PMD) for Observing Cerebral Blood Flow and Tracking Emboli", Ultrasound in Medicine and Biology, vol. 28, No. 1, 2002. pp. 49-57.

Kisslo J.A., et al., "Color Flow Imaging", Echo inContext, Duke Center for Echo, www. echoincontext.com/doppler04/doppler04_01.asp, Duke University Medical Center, 2000. 30 pages.

Alexandrov, A.V. et al., "Insonation Method and Diagnostic Flow Signatures for Transcranial Power Motion (M-Mode) Doppler", Journal of Neuroimaging, vol. 12, No. 3, Jul. 2002. pp. 236-244.

* cited by examiner

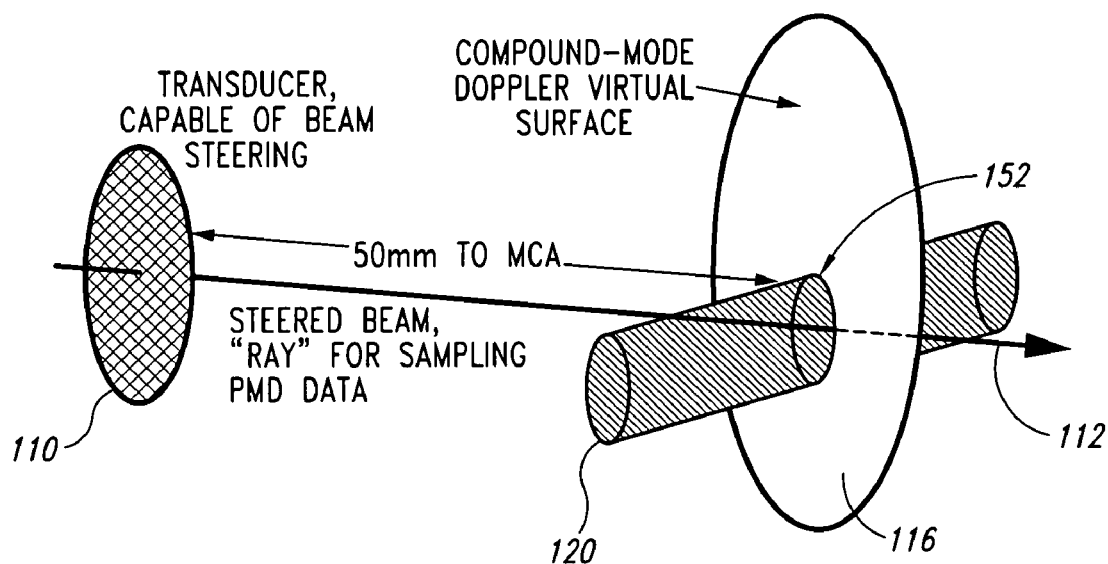
*Fig. 1A*
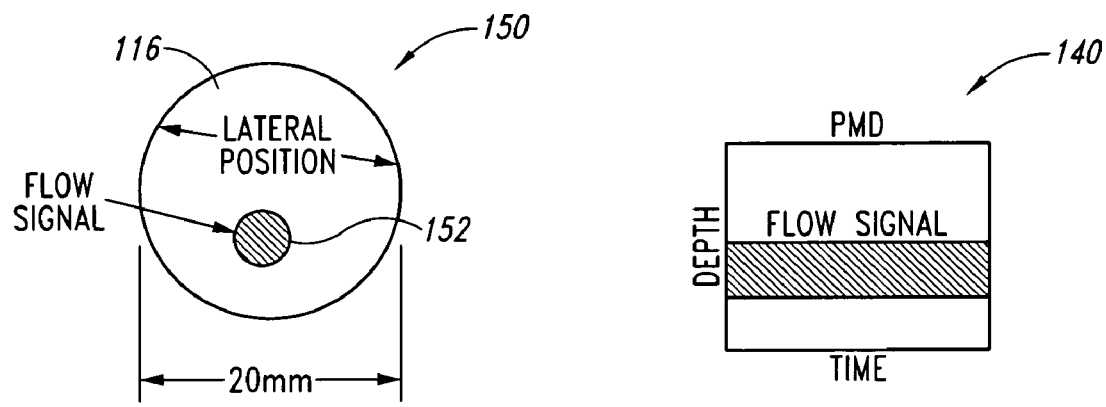
*Fig. 1B*
*Fig. 1C*

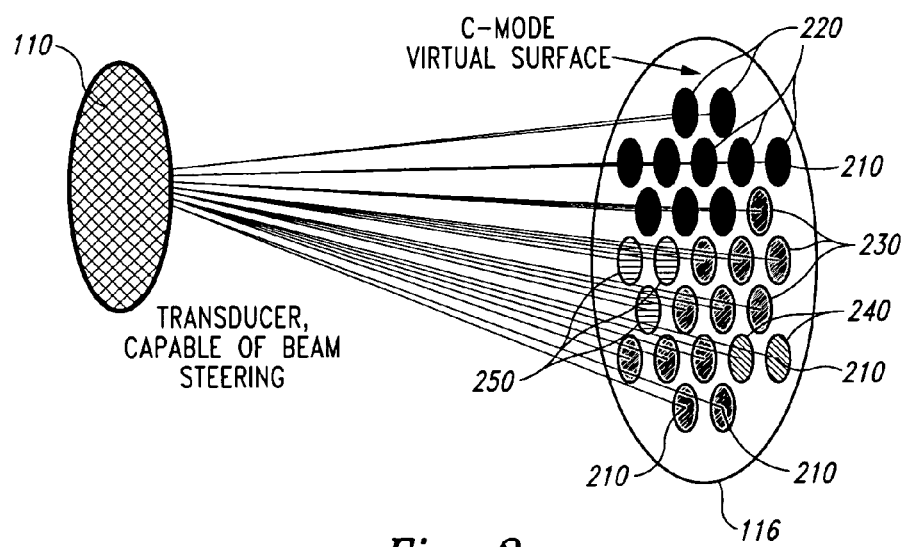
Fig. 2
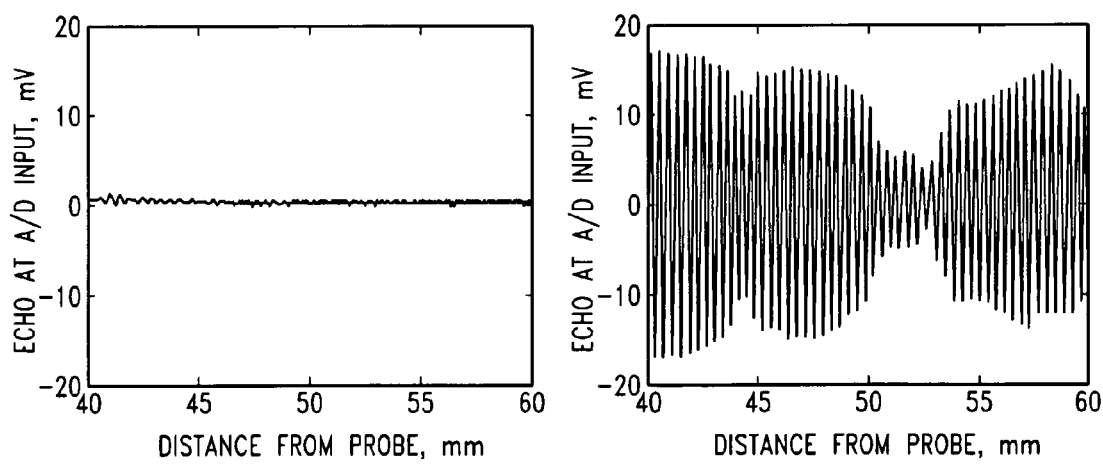
Fig. 3A
Fig. 3B

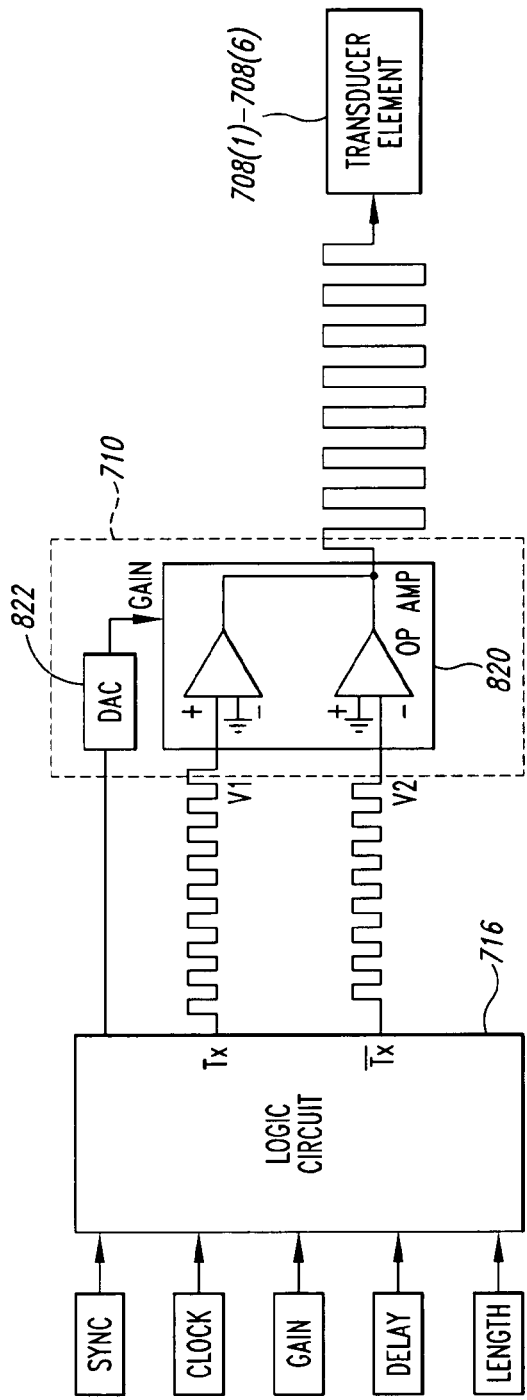
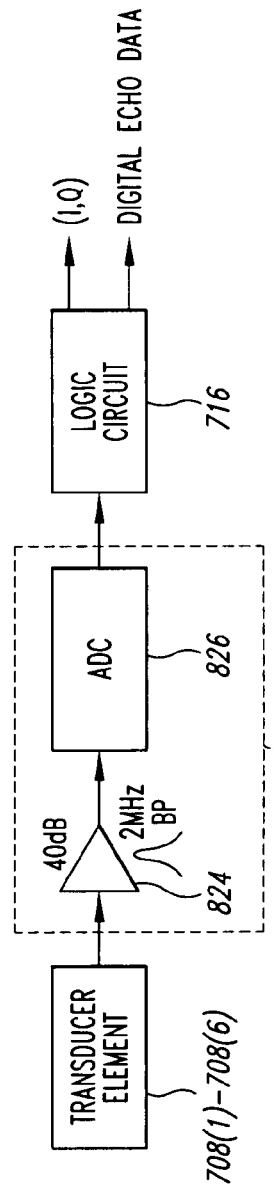
Fig. 8A
Fig. 8B

MEDICAL DOPPLER ULTRASOUND SYSTEM FOR LOCATING AND TRACKING BLOOD FLOW

STATEMENT AS TO GOVERNMENT RIGHTS

The disclosed invention was made with support from the United States Government, which has certain rights in the invention pursuant to Grant No. 1R43NS046055-01 awarded by the National Institutes of Health.

TECHNICAL FIELD

This invention relates generally to medical monitoring and diagnostic devices, and more particularly, to a medical Doppler ultrasound apparatus and method for automatically locating and tracking blood flow to enable monitoring of the blood flow in a patient.

BACKGROUND

The devastation that stroke inflicts is easily found in the medical literature: stroke strikes someone in the United States every 45 seconds and kills someone every three minutes. Each year about 700,000 people suffer a stroke. About 500,000 of these are first attacks. Of all strokes, 88 percent are ischemic, nine percent are intracerebral hemorrhage, and three percent are subarachnoid hemorrhage. The Framingham Heart Study showed that, six months after their strokes, 50 percent of ischemic stroke survivors studied over age 65 had some hemiparesis, 30 percent needed help walking, 26 percent were dependent for daily living, and 19 percent had aphasia. Twenty-six percent were institutionalized. Eight to twelve percent of ischemic strokes are fatal within 30 days. As the mean age of the population increases, the incidence of stroke is projected to increase. Stroke clearly compromises quality of life for its victims and for society at large. In economic terms, the estimated total cost of stroke in the United States in 2004 is $53.6 billion. Direct costs include $26.5 billion for hospital and nursing home stays, $2.7 billion for physicians and other professionals, $1.1 billion for drugs and other medical durables, and $2.7 billion for home health care. Indirect costs are estimated at $6.1 billion in lost productivity due to morbidity and $14.5 billion in lost productivity due to mortality. For Americans age 40 and older, 1995 data showed the average in-hospital and physician costs were $11,010 for a stroke and $4,940 for trans-ischemic attack ("TIA").

Although transcranial Doppler ("TCD") ultrasound has been available for many years as a standard diagnostic modality, and has been shown to have utility in the hands of a skilled user for assessing and monitoring the basal cerebral arteries in the early stroke patient, it has not been widely used in this capacity. This is in part because the demand for this sort of assessment is a recent phenomenon accompanying the advent of thrombolytic therapy, and in part because TCD is difficult at best for the emergency medicine physician or nurse to perform and interpret. In elderly populations, where the technology is greatly needed, frustrating time is consumed in finding signals in many patients. Locating the signal is difficult because of the need to laterally explore each depth one step at a time with single-gate TCD equipment, until flow signals are acquired. Searching for flow can be a tedious and perplexing task. Once a flow signal is acquired, it is confirmed by considering the associated depth, the approximate aim of the probe, and tracing the signal to adjacent vessels as depth is varied to verify the user is indeed on the appropriate vessel. Successful utilization of single gate analog transcranial Doppler is not generally available outside vascular laboratory personnel, and even these ultrasound experts have very mixed reactions to TCD because of the above mentioned difficulties. In summary, these factors combine so that there is a lack of utilization of TCD capabilities in triage and monitoring, which is witnessed by the relatively minor presence of TCD in emergency departments across the United States.

The benefits of rapid and easy to perform assessment of cerebral hemodynamics in the early presentation of a patient with suspected stroke are tremendous, both for the admitting physician and the patient facing a potentially debilitating or fatal stroke. For the physician, there is the early recognition of pathology from hemodynamic observations, such as ischemic blockage, its location, and the accompanying option of thrombolytic therapy. Studies have shown that an untreated occlusion of the middle cerebral artery presents a very poor prognosis for the patient. Hence, knowing about it as soon as possible maximizes the potential for positive intervention. For example, after initiating thrombolytic therapy, monitoring can determine the point in time at which thrombolytic therapy re-establishes perfusion, presenting the possibility of termination of successful thrombolysis in order to minimize risk of bleeding associated with thrombolytic drugs. For the patient, "time is brain." The success of aggressive therapy such as thrombolysis is partly dependent on its application in the first three hours after stroke onset. These benefits will be appreciated in the emergency department and by the patient to the degree that the assessment of cerebral hemodynamics is rapid and easy to perform.

Recently, a digital Doppler platform has been developed by Spencer Technologies in Seattle, Wash. in which up to 33 sample gates can be simultaneously processed into a "color" m-mode image. The color in the m-mode image is a function of Doppler signature power and detected velocity, in that increases in backscattered power cause the colors, red or blue, to become more intense. The digital Doppler platform is referred to as Spencer Technologies' Power M-mode Doppler ("PMD"). Showing power in this fashion conveys to the user when the Doppler beam is well aimed—that is, intensity of color increases with volume of moving blood in the Doppler sample volume and this indicates when the beam is centered on the blood flow. Thus, the color m-mode display of an ultrasound system having PMD capability provides medical professionals who do not have expertise in ultrasound with a mechanism for easy location (by the operator) of the middle cerebral circulation. A more detailed description of PMD ultrasound systems can be found in U.S. Pat. No. 6,196,972 to Moehring, issued Mar. 6, 2001 and assigned to Spencer Technologies.

Displaying color as a function of signal power at multiple depths offers advantages for an examiner to locate a temporal bone window, or an "acoustic window," without limiting interrogation to a single selected depth. When employed in assessment of patients at various vascular laboratories, the sonographers reported that PMD TCD was easier to use since it was no longer necessary to seek a window by changing depth. Also they found it unnecessary to listen for a Doppler sound. In fact, an ultrasound system having PMD capability enabled them to first find the optimal temporal window on the PMD display and then to adjust the gate depth for audible spectral display using the PMD depth scale. The PMD system allowed the examiner to find the temporal window without audible Doppler sounds and therefore avoid crashing sounds of probe application to the head. During intraoperative monitoring, the sonographers maintained their position on the window using the color signals present in the PMD image as a guide. When the flow signals were accidentally lost during surgical monitoring, these could be recovered by repositioning the transducer using the PMD display as the only feedback. Therefore, the significant problem of single gate TCD, that is, frustration in locating difficult windows, was reduced.

Although PMD provides an easy method for aiming the Doppler probe, the task of locating acoustic windows and underlying blood flow is still left to the operator when using the PMD system. Thus, although the development of the PMD platform mitigated the problems related to needing highly skilled operators to operate single-gate TCD equipment, the problems are nevertheless still present to some degree.

SUMMARY

One aspect of the invention provides a system and method for processing echo signals in a Doppler ultrasound system from a region of interest. An ultrasound beam is electronically steered to deliver ultrasound to and receive echo signals from the region of interest. The region includes a plurality of sample locations. Each location has an associated beam axis and at least two different planes are defined in which two or more of the beam axes lie. The echo signals for each sample location are processed to extract Doppler shift signals and Doppler shift data representing the Doppler shift signals are generated.

In another aspect of the invention, a system and method for locating blood flow in a region of interest using a Doppler ultrasound system having a multi-element transducer is provided. An ultrasound beam is steered to deliver ultrasound to and receive echo signals from a plurality of sample locations. The plurality of sample locations are spatially arranged across the region of interest in two lateral dimensions relative to a reference beam axis extending from the multi-element transducer. For each sample location, echo signals are processed to extract Doppler shift signals and generate Doppler shift data, which is accumulated for the plurality of sample locations. Based on the Doppler shift data accumulated for the plurality of sample locations the presence of blood flow in the region of interest is determined, and the location in the region of interest at which the presence of blood flow is detected is identified.

In another aspect of the invention, a system and method for monitoring blood flow in a region of interest using a Doppler ultrasound system having a multi-element transducer is provided. Blood flow in the region of interest is located and a vector identifying the location of blood flow is defined. Ultrasound is delivered to the location of the blood flow and first echo signals are received from the location of the blood flow in accordance with the vector. The first echo signals from the location of the blood flow are processed to determine Doppler signal strength and a blood flow velocity toward the probe. The vector identifying the location of the blood flow in the region of interest is updated and ultrasound is delivered to the location of the blood flow in accordance with the updated vector. Second echo signals are received from the location of the blood flow in accordance with the updated vector and are processed to determine Doppler signal strength and a blood flow velocity toward the probe.

BRIEF DESCRIPTION OF THE DRAWINGS

FIG. 1A is a diagram of a virtual surface which is transected by a blood vessel and over which an ultrasound beam is scanned. FIG. 1B is a plan view of the virtual surface of FIG. 1A. FIG. 1C is a diagram of a power m-mode image of blood flow of the blood vessel transected by the virtual surface of FIG. 1A.

FIG. 2 is a diagram of a virtual surface constructed in accordance with an embodiment of the present invention.

FIGS. 3A and 3B are diagrams showing ultrasound echoes from ultrasound delivered from an ultrasound probe positioned at two locations on the skull of a patient.

FIG. 8A is a functional block diagram of a transmit circuit of the DSP platform of FIG. 7 according to an embodiment of the invention. FIG. 8B is a functional block diagram of a receive circuit of the DSP platform of FIG. 7 according to an embodiment of the invention.

DETAILED DESCRIPTION

Figure 4A:
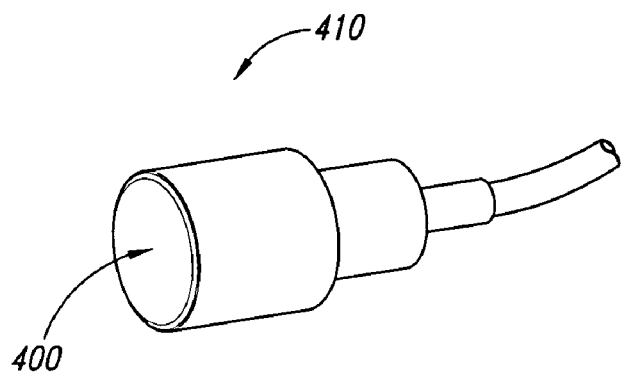
FIG. 4A is an isometric drawing of an ultrasound probe and FIG. 4B is a plan drawing of a multi-element transducer according to an embodiment of the invention included in the probe of FIG. 4A.

When monitoring motion with Doppler ultrasound, such as monitoring blood flow or tissue motion, it is desirable to obtain information that provides high time resolution of acquired signals and has minimal or no time gaps when observing the motion of interest. This generally occurs when the ultrasound beam is aimed in the same direction as the blood flow or tissue motion. As a result, non-scanning ultrasound devices are typically used in these applications where the ultrasound is not used to scan other regions, but is continually aimed at the region of interest during monitoring. Examples of non-scanning ultrasound devices are power M-mode Doppler ultrasound devices, which are described in U.S. Pat. Nos. 6,196,972 and 6,616,611 to Moehring, incorporated herein by reference.

Although observing blood flow or tissue motion can be accomplished with a non-scanning ultrasound device, as previously discussed, a first step of actually locating the target typically requires considerable skill in operating the equipment. As a result, the time required to initially locate the target for monitoring can vary signficantly based the ability of the operator. For example, in a TCD application, an understanding of where to search for an acoustic window in the skull, and the appropriate aiming of the probe during this search process to discover underlying blood flow is highly dependent on the skill and experience of the operator since the operator has little feedback indicating the direction and position of the ultrasound beam relative to the blood flow.

Embodiments of the present invention are directed to a Doppler ultrasound system and a method for locating and tracking blood flow or tissue motion of interest. Included are various embodiments that can be used in TCD applications as a tool for rapid detection of acoustic windows in the skull and underlying blood flow that feeds the cerebral circulation. Generally, however, these embodiments, as well as others, can be used to locate blood flow or tissue motion of interest, and then observe or monitor blood flow or tissue motion continuously. Other embodiments further provide feedback that can be easily understood by an operator to assist in locating and tracking blood flow or tissue motion of interest. It is foreseen that various embodiments of the present invention can be utilized in various applications and environments to quickly locate and track blood flow of interest, such as, monitoring blood flow in basal arteries in the brain, including the middle cerebral artery, the anterior cerebral artery, and the posterior cerebral artery, the carotid siphon and/or the ophthalmic artery as seen through the orbit, the vertebral arteries and the basilar artery as seen through the foramen magnum. For example, using an ultrasound system according to one embodiment of the invention, it is possible for an anesthesia technologist to apply a probe preoperatively and the anesthesiologist, during the surgical procedures, to utilize the information obtained by the system in managing cerebral perfusion and advising the surgeon of dangerous embolic activity. Another example application is in the vascular lab setting, where diagnostic tests such as microembolism monitoring, evaluation of collateral channels, head-turn syncope, bubble test for patent foramen ovale, evaluation of stenosis in any major vessel supplying the brain with blood, and vasospasm mapping may be facilitated using an ultrasound system according to an embodiment of the invention. In other embodiments, tissue motion of interest can be quickly located and tracked, such as monitoring motion of the tympanic membrane, and assessing/monitoring brain tissue motion.

Urgent clinical settings, such as the emergency department, the hospital patient rooms, the operating rooms, and the vascular laboratory, may also benefit from a Doppler ultrasound system according to an embodiment of the invention. For example, an acute stroke patient can be followed from the emergency department to the hospital room without interrupting the monitoring of cerebral arterial blood flow. In the hospital environment nurses and other paramedical personnel can be taught to apply the probe and interpret the information along with other monitoring parameters. During cardiopulmonary bypass, carotid endarterectomy, and orthopedic surgery, the ability to locate and track a signal from the middle cerebral artery will eliminate the need for a special technologist whose cost has been an impediment to use of TCD hemodynamic and embolic information.

Certain details are set forth below to provide a sufficient understanding of the invention. However, it will be clear to one skilled in the art that the invention may be practiced without these particular details. Moreover, the particular embodiments of the present invention described herein are provided by way of example and should not be used to limit the scope of the invention to these particular embodiments. In other instances, well-known circuits, control signals, timing protocols, and software operations have not been shown in detail in order to avoid unnecessarily obscuring the invention. Embodiments of the invention described below are directed to application in monitoring cerebral blood flow. However, some or all of the aspects of embodiments described herein can be utilized for monitoring blood flow, generally, as well as monitoring tissue motion of interest.

Several embodiments are described below to illustrate various aspects of the present invention. For example, images of compound-mode Doppler virtual surfaces that can be used to obtain visual feedback information for locating blood flow or tissue motion of interest are described below. One compound-mode Doppler virtual surface described is constructed from a plurality of sample locations distributed over a region of interest. The sample locations are interrogated by electronically steering ultrasound in the direction of the different sample locations. A multi-element transducer and a Doppler ultrasound system having multi-channel Doppler digital signal processing providing electronic ultrasound beam steering is also described below. Following the description of the ultrasound system, an algorithm for locating blood flow or tissue motion of interest is described, along with a discussion of a minimum variance estimation technique that can be utilized in a locating algorithm. Additionally, an algorithm for locating an acoustic window through which cerebral blood flow can be monitored is also described and the locating algorithm is described for the specific application of locating cerebral blood flow. An algorithm for tracking the located blood flow is described in combination with the locating algorithm. However, the tracking aspect does not need to be combined with the locating aspect. A discussion of various embodiments of multi-element transducers follows the discussion of the locating algorithm, which is followed by a description of an embodiment that combines various aspects of the invention to provide locating, tracking, and monitoring of blood flow.

In one embodiment of the invention, information related to a spatial relationship between a PMD image, such as that provided in the Doppler ultrasound device described in the aforementioned U.S. Pat. Nos. 6,196,972 and 6,616,611, and an image of a compound-mode Doppler "virtual" surface is provided to an operator. Compund-mode is an older term in the development history of medical ultrasound and refers to "compound scan" imaging, which has been used to observe tissue at a fixed depth from the probe. The surface is virtual in that the surface does not physically exist, but represents a region to which ultrasound is delivered and from which Doppler information is obtained.

An example of the spatial relationship between PMD, a style of m-mode imaging, and an image of a compound-mode Doppler virtual surface in the context of observing blood flow in the middle cerebral artery ("MCA") 120 is illustrated in FIGS. 1A-1C. In FIG. 1A, an ultrasound beam (not shown) emanating from an ultrasound probe 110 has a central axis 112. Various locations along the axis 112 can be sampled for blood flow information by evaluating the echoes for motion at points distributed all along the axis 112. As shown in FIG. 1A, a constant-depth spherical shell at 50 mm depth having a fixed arc length spanning about 20 mm intersects the MCA 120. The shell represents a compound-mode Doppler virtual surface 116 that is interrogated by ultrasound to obtain information for a region of interest. In one embodiment on the invention, the virtual surface 116 is scanned for Doppler (blood flow) signals and a circular image 150 representative of the virtual surface 116 presented to the user, as shown in FIG. 1B. When blood flow from the MCA 120 intersects the virtual surface 116, a spot representing a blood flow signal 152 appears on the circular image 150. The blood flow signal 152 has a color (color not shown in FIG. 1B) according to the direction of motion and has an intensity proportional to the strength of the Doppler signals. For example, a red color can be used to represent blood flow toward the probe 110 and a blue color can be used to represent blood flow away from the probe 110. A PMD image 140, shown in FIG. 1C, is constructed for the blood flow signal 152 and illustrates blood flow at a 50 mm depth over time in a PMD format. As will be explained in more detail below, the use of a compound-mode Doppler virtual surface 116 can also be used to quickly locate a good acoustic window through bone and locate blood flow.

In the present embodiment, a compound-mode virtual surface 116 having a 20 mm diameter is provided at a 50 mm depth. To provide coverage over a 20 mm diameter, beam steering is employed to detect blood flow at points across the virtual surface 116. A relatively narrow ultrasound beam is steered to various "look directions" 210 across the virtual surface 116, which are shown in FIG. 2. Generally, each of the look directions corresponds to a sample location in the region of interest. Information obtained from a series of transmit bursts at each of a series of the look directions 210 is used to detect blood flow passing through the virtual surface 116. The series of look directions 210 essentially "tile" the virtual surface 116 so that an array of points in the 20 mm virtual surface 116 are interrogated with ultrasound. The data which is acquired at a given look direction 210 is constructed from a series of transmit bursts, and can be used to calculate the angular spectrum of the Doppler signal, as will be described in more detail below. The angular spectrum of the Doppler signal in the local neighborhood of a given look direction 210 can be used to process greater angular resolution for flow signal location, thereby adding detail to the image of the virtual surface 116 greater than that illustrated in FIG. 2.

The data from the look directions 210 are processed and combined in a montage that displays the data concurrently. While the image is displayed, new data can be acquired and processed to update the image. Data acquisition sufficient to construct an image that provides real-time feedback to an operator holding the probe is desirable. Generally, updating an image of the virtual surface 116 at ten frames per second, which corresponds to one frame every 100 ms, should provide acceptable feedback and should further provide sufficient time to obtain data from enough different look directions 210 to adequately survey the virtual surface 116.

As shown in FIG. 1B, the surface 116 is a circular spherical shell at a constant radius from the probe 110. However, the surface 116 can have different surface features and shapes without departing from the scope of the present invention. For example, in one embodiment, the surface 116 can be rectangular shaped rather than circular. The surface 116 can be planar (variable radius from the probe 110) rather than a spherical shell (constant radius from the probe 110). The surface 116 can be tilted with one edge at a different distance from the probe 110 than the opposite edge. The surface 116 may be curved in one-dimension and flat in the second dimension.

Additionally, the look directions, which generally define sample locations of the surface 116, have been shown having a certain dimension and spatial arrangement on the surface 116. Both of these characteristics can be modified without departing from the scope of the present invention. It will be appreciated, however, that it is desirable for the sample points to have sufficient density to survey the surface 116 for blood flow in the region of interest. Generally, the sample locations of the surface 116 have an associate beam axis that generally defines a direction of the sample location. As a result of distributing the sample locations over a region having lateral extent in two-dimensions relative to the probe, there are at least two different planes that are defined which have two or more beam axes lying in the respective plane. In contrast, B-mode ultrasound is accomplished with more than one sample point (indeed, many) per beam steering direction or source position. The depth direction of B-mode produces one dimension of the B-mode image at no additional time expense than listening sufficiently long to echoes from each outgoing pulse. The scanning or imaging forming the surface 116 utilizes two degrees of lateral or angular freedom and generally requires more ultrasound pulses to scan the surface 116.

The value assigned to a sample point on the virtual surface 116 is a function of the ultrasound echoes sampled from the ultrasound beam directed to that particular location. As will be explained in more detail below, the value is derived from the extracted Doppler shift signals along the beam, and may be signal amplitude (or power) at the depth of the surface 116, the time rate of change of phase of the signal (velocity) at the depth of the surface 116, a frequency domain property such as integrated power associated with velocities above a threshold and at the depth of the surface 116, or a maximum velocity detected along the beam direction, or a combination of some or all of the above. The value assigned may be a scalar or a vector. The value assigned to a sample point may subsequently be used in forming an image to be displayed to an operator, or subsequently be used for automatic location or monitoring or tracking of blood flow, as will be described below. If used to form a graphical image for the user, the value may do so in different ways, for example, a scalar may be depicted simply by image intensity, while a vector may be depicted by image intensity and color.

In the present embodiment, the virtual surface 116 is constructed from a plurality of look directions 210 in part due to constraints in using ultrasound in a TCD application. That is, in the present example of detecting blood flow in MCA, which is typically at a 50 mm depth when the probe is on the side of the head at the temporal bone, various beam characteristics of the ultrasound beam are a function of the dimension of the probe at the surface of the skull. A narrow beam diameter at 50 mm depth results from constraints of using ultrasound in TCD and dictates the number of look directions to "tile" the virtual surface 116. For example, one constraint is that of maintaining a thermal index cranial ("TIC") at a level below that of concern for increased temperature in the temporal bone. The constraint predicates using low amplitude ultrasound combined with a wider exposure area (transducer area) to accomplish a useful acoustic intensity at the depth of interest. As a result, a beam having a relatively narrow beam profile is generated. Additionally, using an ultrasound beam having a diameter at the depth of interest that is similar to or smaller than the cross section of blood flow to be monitored is desirable. A 13 mm diameter probe transmitting at 2 MHz ultrasound has a transverse dimension at 50 mm depth that is similar to the diameter of the MCA, which is typically about 3 mm in diameter. However, the resulting narrow beam is inappropriate for assessing the entire virtual surface 116 with a small number of transmit bursts and is generally limited to being aimed in essentially one direction at a given time. Thus, a series of transmit bursts at a plurality of look directions 210 are used to detect blood flow across the virtual surface 116.

The ultrasound data acquired at each of the look directions 210 is interpreted and categorized into three categories for display: (1) no signal is present because of lack of ultrasound transmission through bone, (2) a signal present because ultrasound is successfully transmitted through bone, but there is no blood flow detected, and (3) blood flow is detected. The first category corresponds to a case where the look direction 210 is not through an acoustic window. The second category corresponds to the case where the look direction 210 is through an acoustic window, but the presence of tissue is detected in the particular look direction 210 and not blood flow. Each of the three categories can be displayed differently in an image of the virtual surface 116. As shown in FIG. 2, the first category is shown as a black spot on the image, for example, look direction 220. The second category is shown as a gray spot on the image, as for look direction 230. The third category is shown as a spot on the virtual surface 116 having a color based on the direction of blood flow detected, as for look directions 240 and 250 (color not shown in FIG. 2).

In identifying which look directions 210 are aimed through an acoustic window or not, the ultrasound reflections are analyzed. FIGS. 3A and 3B show examples of ultrasound reflections corresponding to between 40 and 60 mm depth from the probe. FIG. 3A shows reflected ultrasound signals when the probe is placed on the forehead of a human subject, which is an example of positioning the probe over a region that is not an acoustic window. As shown in FIG. 3A, there is no ultrasound transmission through the bone and a poor reflected signal is detected at the depth of interest. In contrast, FIG. 3B shows reflected ultrasound signals for the case when the probe is placed on the temporal bone, which typically corresponds to a location over or near an acoustic window. As shown in FIG. 3B, strong ultrasound reflections are observed, with the signal shown representing the convolution of the ultrasound transmit burst with the tissue backscatter function from a region including brain tissue.

In categorizing the reflected ultrasound signals, as previously discussed, the two signals can be differentiated from each other using a variety of techniques, including energy thresholding. For example, if the signal level at a desired depth falls below a threshold, the data from the look direction 210 can be categorized in the first category. The corresponding look direction 210 can be colored in the image of the virtual surface 116 to indicate that there is no transmission through bone, which is black in the present example. However, if the signal level at a desired depth is above a threshold, then the data from the look direction 210 can be categorized in the second category and can be colored in the image to indicate transmission through bone, which is gray in the present example. If the signal level is above a threshold and there is Doppler signal energy which is also above a threshold, the data from the look direction 210 can be categorized in the third category and can be colored to indicate detected blood flow. As previously mentioned, red can be used to represent blood flow towards the probe and blue can be used to represent flow away from the probe. Additionally, the intensity of the coloration can depict the strength of the backscattered Doppler signal. That is, when the ultrasound from the probe goes through a "good" acoustic window at the skull, the blood flow signal will appear intense and when the ultrasound goes through a "poor" acoustic window, the blood flow signal 152 will appear dull.

An example of an ultrasound system 600 (FIG. 6) according to an embodiment of the present invention that provides the features of locating and tracking blood flow is described below. The particular embodiment will be described as utilizing a multi-element transducer having a six transducer elements. Those ordinarily skilled in the art however, will obtain sufficient understanding from the description provided herein to practice the invention with multi-element transducers having greater or fewer transducer elements than described below to the specific embodiment. The embodiment using the six-element transducer provides an example which illustrates various aspects of the present invention that can be applied in alternative embodiments, such as those using different multi-element transducers, using a different number of transducer elements, or being utilized in different applications.

Those ordinarily skilled in the art will further appreciate that the numerical processing employed to locate and track blood flow or tissue motion, as described below, can be generalized to ultrasound systems having transducers with different numbers of elements. Thus, the six-element transducer system described below for specific applications such as observing blood flow in the MCA can be modified without departing from the scope of the present invention. Such modifications include those made in light of geometric and physiological considerations. Examples of these considerations include the distance from the probe to the anatomical region to be observed, the size of the structure to be observed, the lateral distance at depth of possible locations of the structure to be observed, the direction and speed of the motion to be observed, and the like. These considerations translate to design parameters such as array size, element size, pulse repetition frequency, number of look directions, ultrasound frequency, number of pulses per look direction, and array apodization, as will be described in more detail below.

Figure 4B:
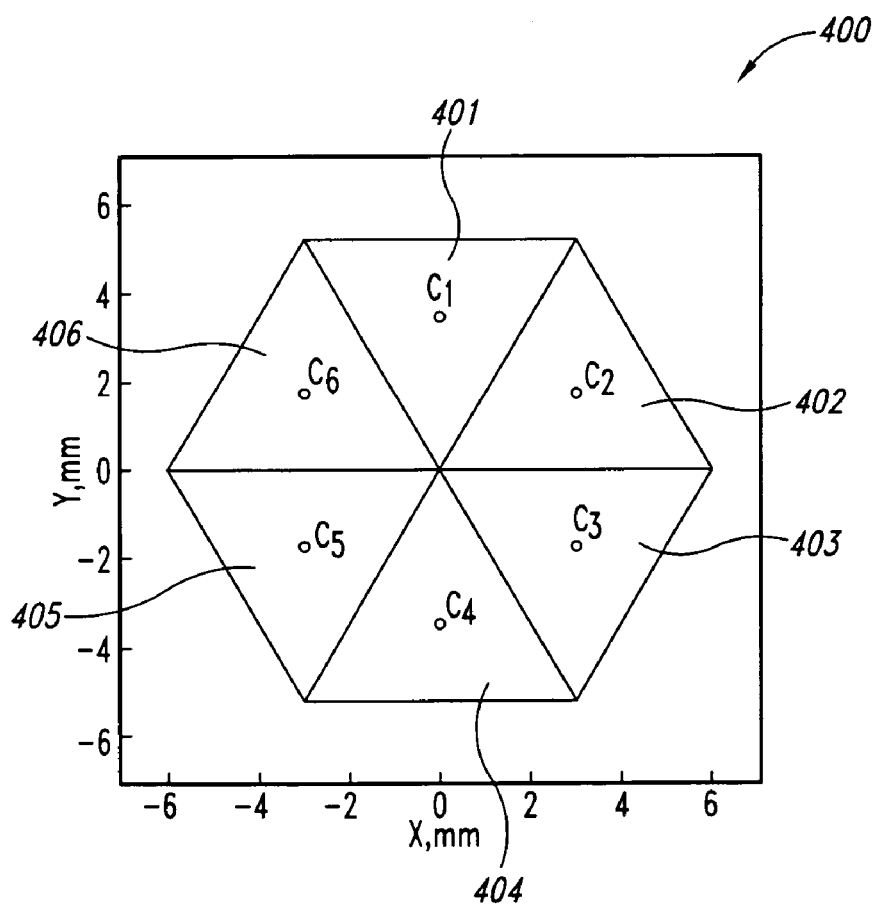
Figure 5A:
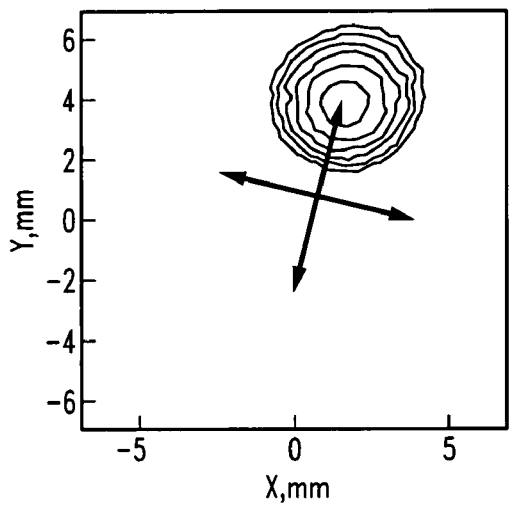
FIGS. 5A-5D are acoustic intensity maps of steered ultrasound beams delivered by the probe and multi-element transducer of FIGS. 4A and 4B.
Figure 5B:
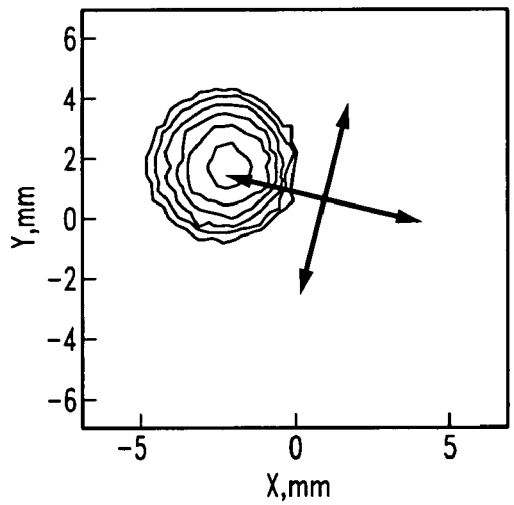
Figure 5C:
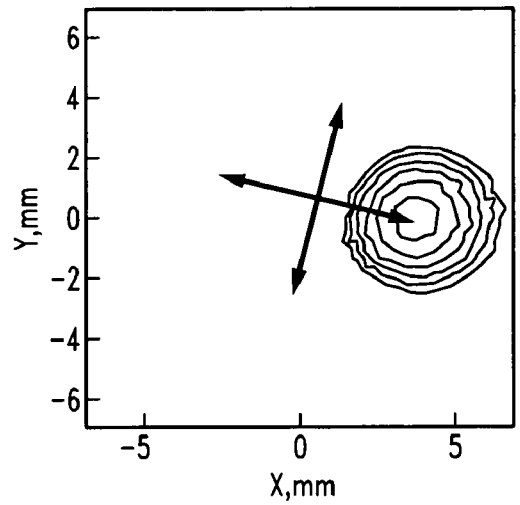
Figure 5D:
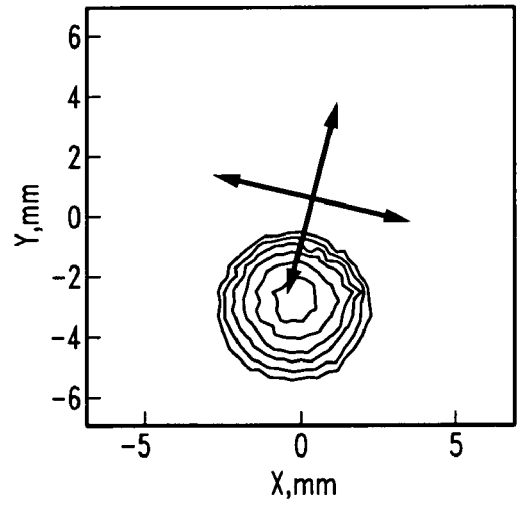

FIG. 4A illustrates an ultrasound probe 410 having a multi-element transducer 400 according to an embodiment of the present invention. The arrangement of transducer elements of the multi-element transducer 400 is shown in FIG. 4B. A transducer as shown in FIG. 4B was constructed by Blatek (State College, Pa.). The transducer 400 includes six triangular transducer elements 401-406 arranged in a hexagonal shape. The size of the hexagon is similar to the footprint of current single element transcranial Doppler probes, that is, measuring approximately 10 mm between two parallel sides of the hexagon. The hexagonal array is inscribed inside a circular package. All of the transducer elements are matched to 50 ohms real. Composite elements are used for the transducer elements to maximize sensitivity and minimize cross talk. A quarter wave matching layer is placed on the front of the array to maximize sensitivity on receive. A Faraday shield is placed around the entire probe and connecting cable. The transducer 400 is capable of providing an unsteered transmit beam of 0.7 W/cm$^2$ (spatial peak temporal average intensity using 16 cycle bursts at 8 kHz pulse repetition rate).

The transmit beam profile of the transducer 400 generally exhibits circular symmetry and provides a 2.4 mm spotsize at the −3 dB intensity level at a depth of 50 mm. FIGS. 5A-5D illustrate delivery of a beam steered to four different positions relative to a normal axis and having beam shape characteristics at the four different locations that are nearly identical. The beam is shown in FIGS. 5A-5D by the generally concentric circles, with each larger circle representing a region of lower beam intensity. The center of the beam can be electronically positioned up to 5 mm from the normal axis at 50 mm depth using a DSP platform that is described in more detail below. The normal axis (extending perpendicular to the plane of the page with depth increasing into the page) is identified by the intersection of the arrows in each of the four figures. As shown in FIGS. 5A-5D, the ultrasound beam can be successfully steered to provide ultrasound in different directions. Using the beam steering capabilities, a plurality of sample locations corresponding to look directions can be used to survey a region of interest. For example, steering the ultrasound beam can be used to interrogate sample locations across the virtual surface 116 to interrogate a region of interest.

Figure 6:
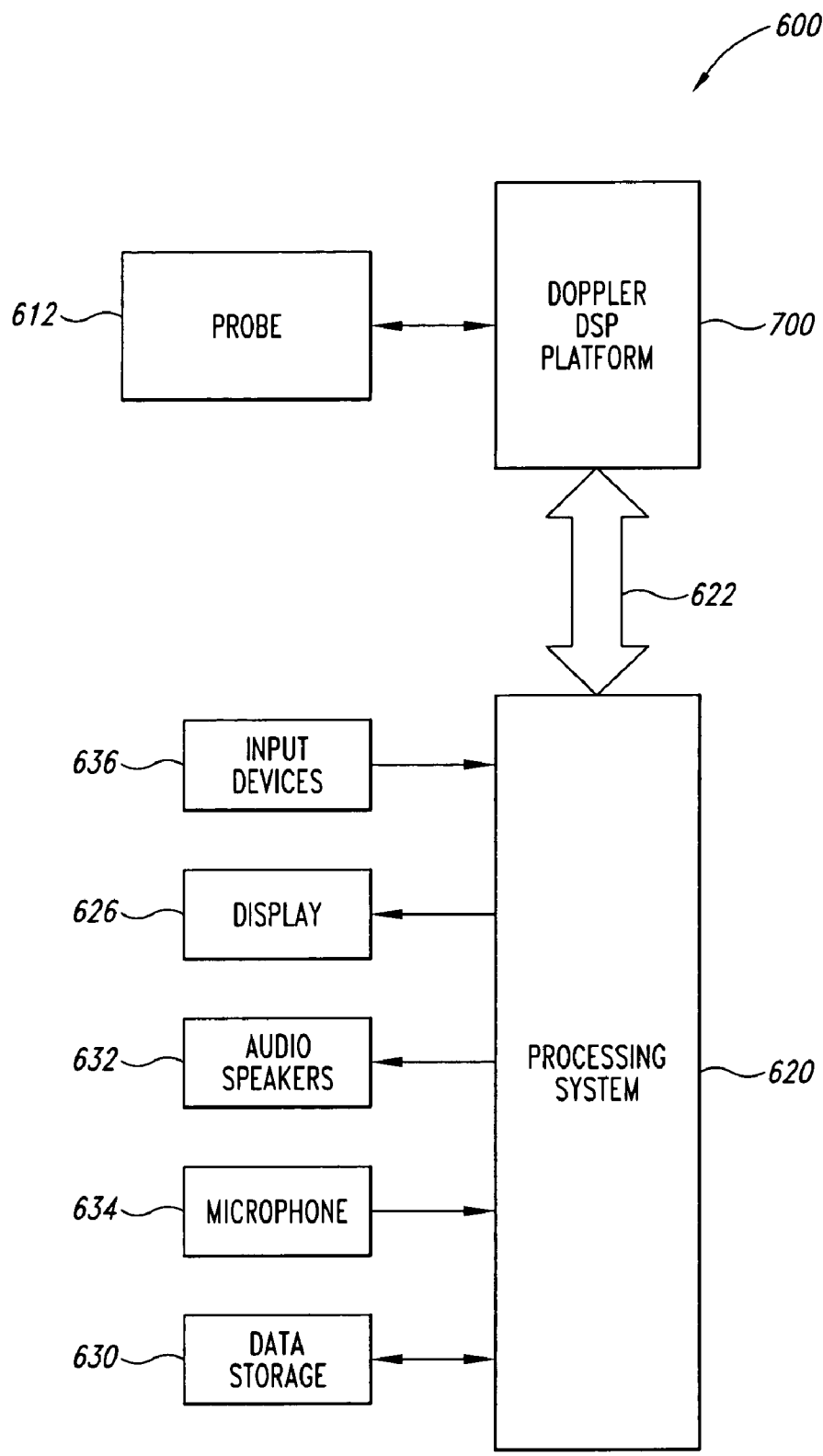
FIG. 6 is a functional block diagram of a Doppler ultrasound system according to an embodiment of the invention.

FIG. 6 is a functional block diagram that depicts the Doppler ultrasound system 600 in accordance with an embodiment of the invention. As will be described in more detail below, the Doppler ultrasound system 600 can be used to electronically steer an ultrasound beam to a plurality of locations in a region of interest to survey the region. For example, the virtual surface 116 (FIGS. 1 and 2) can be constructed through beam steering and Doppler shift signal processing. In this manner, blood flow in the region of interest can be located visually. In alternative embodiments, a locating algorithm is executed to automatically locate blood flow in a region of interest, and in some embodiments, automatically tracked to maintain observation of the blood flow. The ultrasound system 600 includes a multi-channel Doppler DSP platform 700 coupled to a probe 612 having a multi-element transducer (not shown in FIG. 6). The multi-element transducer includes a plurality of transducer elements with independent transmit and receive control of pulse packet phase and amplitude on each element. The probe 410 shown in FIG. 4A and having the arrangement of multi-element transducer 400 shown in FIG. 4B can be substituted for the probe 612. As will be described in more detail below, the DSP platform 700 is configured to perform transmit and receive beam steering by modifying phase and amplitude of the outgoing transmit pulse of each active transducer element and analyzing the receive signals from the steering direction. The receive function for the DSP platform 700 will be described with respect to the present embodiment as utilizing the same set of elements as used on transmit. However, alternative embodiments of the present invention are not limited as such, and different numbers of elements can be used for transmit and receive functions. The DSP platform 700 provides for generating transmit waveforms with variable amplitude and delay to drive the transducer elements of the probe 612, digitizing receive echo signals detected by the transducer elements of the probe 612, and signal processing to generate Doppler shift data representing Doppler shift signals extracted from the receive echo signals.

The DSP platform 700 is coupled to a processing system 620 through a bus 622. The bus 622 can be implemented using conventional computer busses and protocols, for example, the bus 622 can be a universal serial bus ("USB"). The processing system 620 is configured for additional processing of the Doppler shift data provided by the DSP platform 700 and provides the DSP platform 700 with, among other things, commands and data related to electronic beam steering of the transmit and receive signals. Additionally, the processing system 620 executes algorithms for locating and tracking blood flow, as described in more detail below. The processing system 620 can be a host computer system to which the DSP platform 700 is coupled, or alternatively, can represent processing systems included in the DSP platform 700 or in an ultrasound system in which the DSP platform 700 is included for standalone Doppler signal processing, and locating and tracking of blood flow.

The processing system 620 is coupled to a display device 626 for providing visual information and feedback to an operator. The information can be displayed in different formats on the display device 626. For example, for monitoring blood flow in the MCA, a format such as that previously described with reference to FIGS. 1 and 2 can be used. The display device 626 can be a conventional display device now known or later developed, including a flat panel display or cathode ray tube ("CRT") display, which can be integrated with the ultrasound system 600, or is a standalone display device connected to the Doppler ultrasound system 600 or to the processing system 620.

The processing system 620 is coupled to a data storage device 630 to store data to or retrieve data from external storage media. Examples of typical data storage devices 630 include hard and floppy disks, tape cassettes, compact disk read-only ("CD-ROMs") and compact disk read-write ("CD-RW") memories, and digital video disks ("DVDs"). The ultrasound system 600 is also coupled to audio speakers 632 for providing audio information. The ultrasound 600 is further coupled to a microphone 634 for receipt of audible information input by the user, and coupled to one or more input devices 636, such as a keyboard or a mouse, to allow an operator to interface with the processing system 600. Although not shown in FIG. 6, the processing system can include conventional circuits and software for storing the audio and visual data for later playback and viewing.

Figure 7:
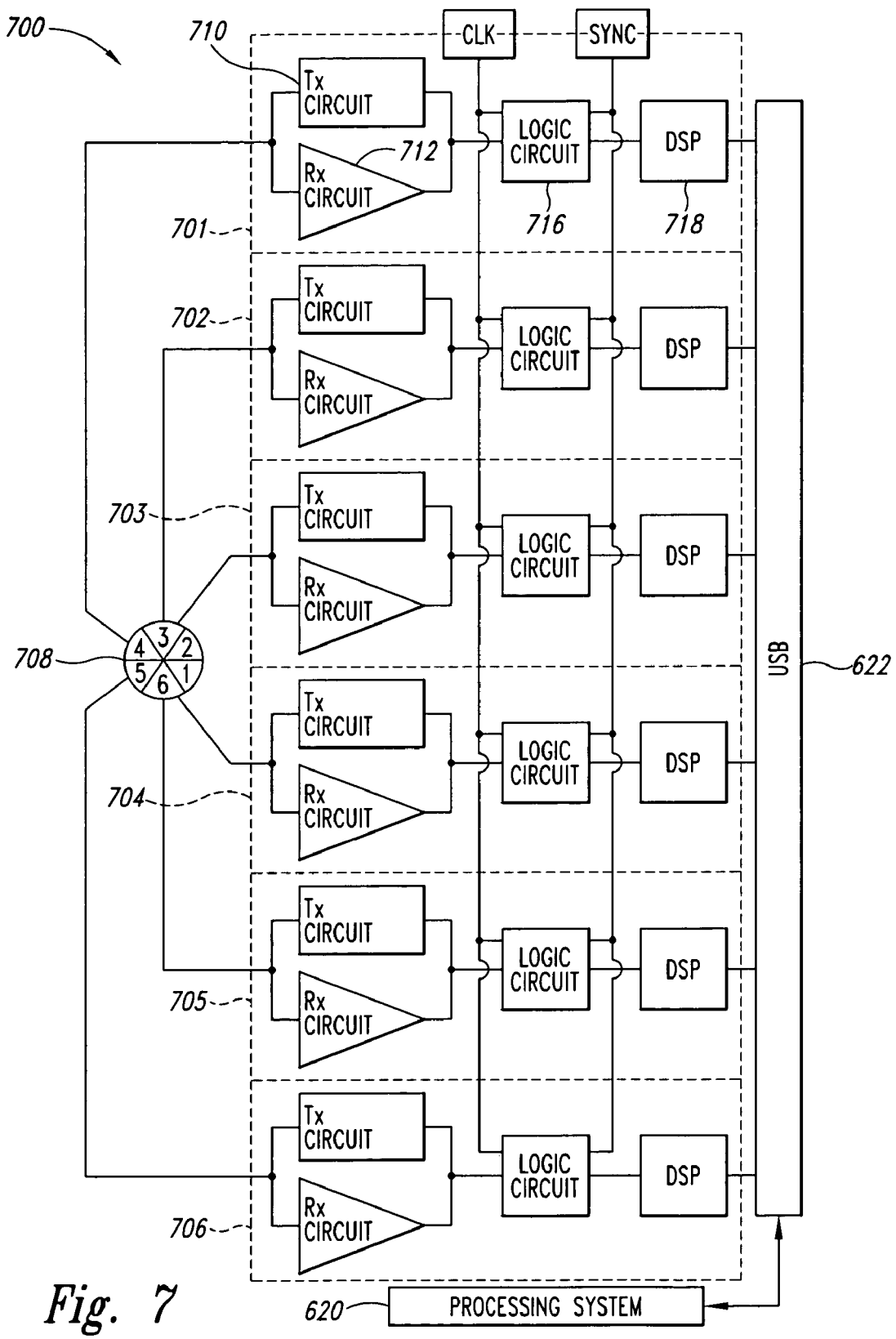
FIG. 7 is a functional block diagram of a digital signal processing ("DSP") platform according to an embodiment of the invention.

FIG. 7 illustrates the DSP platform 700 according to an embodiment of the present invention. The DSP platform 700 includes six TX/RX/DSP-channels 701-706, each of which is coupled to a respective transducer element of a six-element transducer 708 having transducer elements 708(1)-708(6). The transducer 708 is typically included as part of the probe 612 (FIG. 6). Each TX/RX/DSP-channel 701-706 includes transmit and receive circuits 710 and 712, respectively, coupled to a DSP 718 through logic circuit 716. The logic circuit 716 represents a front end processor that is used for performing repetitive tasks in the processing chain. It can be viewed as a link between the analog front end of the TX/RX/DSP-channel represented by the transmit and receive circuits 710 and 712, and the digital environment of the DSP 718. The TX/RX/DSP-channels 701-706 are coupled through the data bus 622 to the processing system 620. As previously discussed, the processing system 620 can represent a host computer system, processing systems included with the DSP platform 700, processing systems included in the ultrasound system 600, or some other alternative processing system. An external clock signal CLK and synchronization signal SYNC are provided to the logic circuits 716 to synchronize operation of the logic circuits 716. The SYNC signal may be generated by a separate circuit, or alternatively, can be generated by the logic circuit 716 of one of the six TX/RX/DSP-channels 701-706 and then passed to the other logic circuits 716 for synchronizing operation of the remaining TX/RX/DSP-channels 701-706.

As previously discussed, the DSP platform 700 is coupled to a multi-element transducer 708, such as the transducer 400 (FIG. 4B). Each transducer element 708(1)-708(6) of transducer 708 has independent transmit and receive control of pulse packet phase and amplitude. In this manner, a transmit beam delivered by the transducer 708 can be electronically steered as shown in FIGS. 5A-5D. That is, the transmit beam can be delivered along an ultrasound beam axis that is off-axis from a normal (i.e., perpendicular) axis of the face of the transducer 708. As known, electronic beam steering can be accomplished by using different time delays and different amplitude weights (apodization) for the waveform applied to each transducer element 708(1)-708(6) when delivering a transmit pulse and receiving echoes. Timing and amplitude of the waveform driving each transducer element 708(1)-708(6) is controlled by the respective TX/RX/DSP-channels 701-706 to perform transmit and receive steering. Note that beam steering is implemented on both transmit and receive. On transmit, the transmit beam is directed to a target, and on receive, the receive signals are analyzed relative to the steering direction.

FIGS. 8A and 8B illustrate the transmit circuit 710 and the receive circuit 712 according to embodiments of the present invention. With respect to the transmit circuit 710 of FIG. 8A, the processing system 620 provides commands for gain, phase (delay associated with steering the transmit beam), carrier frequency, length of the transmit burst and pulse repetition rate to the DSP 718 (FIG. 7). In one embodiment, each transducer is driven to deliver pulsed ultrasound having a carrier frequency of 2 MHz and a pulse repetition frequency of 8 kHz. The DSP 718 provides the appropriate digital commands to the logic circuit 716 to activate a particular mode (i.e., transmit or receive) of operation. The logic circuit 716 generates two digital logic pulse trains V1 and V2 with the specified carrier frequency (divider applied to external clock), pulse repetition rate (initiated by external sync input), and pulse length. The two signals V1 and V2 are appropriately delayed relative to the SYNC signal provided to the logic circuit 716 for the respective TX/RX/DSP-channels 701-706 in order to accomplish electronic beam steering when all active elements are considered together. The two signals are provided to an operational amplifier 820 included in the transmit circuit 710, are added 180 degrees out of phase, and amplified by the operational amplifier 820 according to the gain specified by the processing system 620. The operational amplifier 820 is preferred to provide approximately 40 dB of programmable transmit gain. However, amplifiers having other gain characteristics can be used as well. The specified gain is provided to the logic circuit 716 as digital data, which is converted by a digital-to-analog converter 822 into an analog gain signal applied to the operational amplifier 820. The resulting output signal from the operational amplifier 820 is a square "sinusoid" with center voltage of zero volts. The amplified signal is then applied to a respective transducer element 708(1)-708(6) through a tuning circuit (not shown in FIG. 8A) to drive the respective transducer element 708(1)-708(6) to deliver transmit pulses. When combined, the respective transmit pulses of each transducer element 708(1)-708(6) results in a transmit beam delivered by the transducer 708.

With respect to the receive circuit 712 of FIG. 8B, receive signals detected by a respective transducer element 708(1)-708(6) are provided to a receive amplifier 824 preferably having a fixed gain of approximately 40 dB, and bandpass filtering that has center frequency at 2 MHz and a bandwidth of approximately 300 kHz. In the present example, 2 MHz is the center or carrier frequency for the transmit beam. Other carrier frequencies and corresponding center frequencies can be used as well. As understood by those ordinarily skilled in the art, modifying the carrier frequency may include consideration of the resulting beam geometry, penetration through skull, and transducer element configuration and size.

For each pulse period of ultrasound, echo signals resulting from the bandpass-filtering of receive signals are sampled at four times the carrier frequency by an analog-to-digital converter ("ADC") 826 to provide digital echo data representing the echo signals. In the present example, the sampling frequency of 8 MHz. As shown in FIGS. 7 and 8, each channel includes the same functional blocks. In alternative embodiments, some or all of the functional blocks can be combined into one circuit that is shared or multiplexed for each of the different channels. For example, rather than having an ADC 826 for each channel, a single ADC having sufficient sampling rate can be shared by all of the channels for digitizing echo signals received by the respective channels. Other functional blocks can be combined as well without departing from the scope of the invention.

The echo data are processed by the logic circuit 716 to demodulate the echo signals from a pulse period of ultrasound into Doppler (I,Q) shift samples that stratify the depth range of interest along the ultrasound beam. As known in the art the "I" value represents a measure of a Doppler shift sample along an "in-phase" or "real" axis of the complex plane and the "Q" value represents a measure of the Doppler shift sample at essentially the same time and position, but on a "quadrature" or "imaginary" axis of the complex plane. In addition to the Doppler shift samples, the echo data generated by the ADC 826 are also output by the logic circuit 716. As will be explained in more detail below, the digital echo data, along with the Doppler shift samples, can be processed for identifying a direction for monitoring blood flow.

The Doppler (I,Q) shift samples and the echo data generated by the logic circuit 716 are provided to respective DSPs 718 (FIG. 7), which constructs Doppler shift signals from multiple Doppler shift samples. Each Doppler shift signal is constructed from Doppler shift samples from the same echo depth and across multiple pulse periods. The Doppler shift signals are represented by Doppler shift data that are output by the respective DSPs 718.

Figure 9:
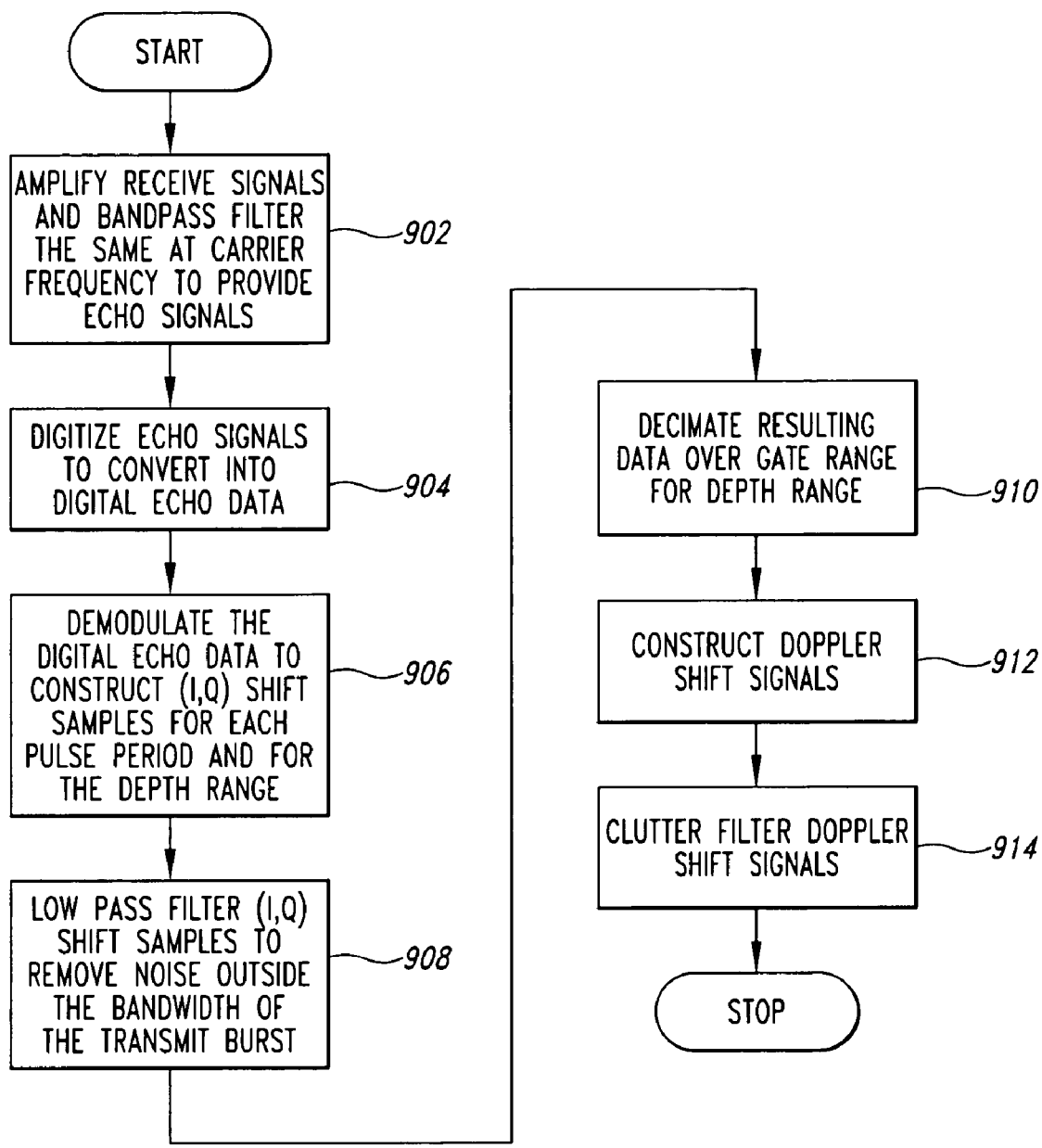
FIG. 9 is a flow diagram of a process for Doppler shift signal processing according to an embodiment of the invention.

FIG. 9 is a flow diagram illustrating the signal and data processing performed by the DSP platform 700 for receive signals. The receive signals are amplified and band-pass filtered at the carrier frequency at step 902. The band-pass filtered signal is then digitized to provide digital echo data representing the receive signal at step 904. The echo data is demodulated at step 906 to generate Doppler (I,Q) shift samples for the depth range that are low-pass filtered at step 908 to remove noise outside the bandwidth of the transmit signal. Demodulation and low-pass filtering are performed within each pulse period. At step 910, the low-pass filtered Doppler (I,Q) shift samples are decimated to carry forward only candidate signals at the depth or at specific depths across a depth range of interest. Doppler shift signals represented by Doppler shift data are constructed at step 912 from the Doppler shift samples from multiple pulse periods. The Doppler shift signals are clutter filtered at step 914 to suppress "clutter" from each Doppler shift signal which can introduce severe artifact into a locating algorithm performed for identifying blood flow.

Suitable methods for demodulating, low-pass filtering and decimating are described in greater detail in the aforementioned U.S. Pat. No. 6,196,972 to Moehring. However, it will be appreciated that other methods can be used as well. In summary, the aforementioned patent describes a demodulation process for generating Doppler (I,Q) shift samples that can be performed through simple subtraction operations operating on each successive quartet of samples of echo data for a pulse period. Each sample corresponds to digital echo data resulting from sampling the signal output by the receive amplifier 824 at four-times the carrier frequency. For a quartet of samples, the third value is subtracted from the first value to produce the real part "I," and the second value is subtracted from the fourth value to produce the imaginary part "Q" of a complex Doppler (I,Q) shift sample for an associated depth. The same operation is performed on all quartets of samples of echo data for a pulse period, with each succeeding quartet of points associated with a location of greater depth. The particular demodulation method blurs the axial resolution by approximately one wavelength of the carrier, but is acceptable in typical applications since one wavelength of the carrier is inconsequential relative to the typical sample volume size associated with medical pulse Doppler ultrasound.

Demodulation into Doppler (I,Q) shift samples is followed by a low-pass filter operation. The low-pass filter operation described in the aforementioned patent involves taking as many as 35 contiguous gate positions bracketing a desired gate depth, within one pulse period, and applying a low-pass finite impulse response ("FIR") filter. The process of low-pass filtering reduces out-of-band noise from a signal which is sampled across successive pulses at a relatively low frequency (i.e., the pulse repetition rate). The FIR filter is applied to the Doppler (I,Q) shift samples spanning the depth range bracketing a gate to construct one Doppler (I,Q) shift sample for each particular gate for the particular pulse period. The desired gate depth or range of gate depths that are output from this process will depend on the application of the Doppler ultrasound system. For example, for monitoring blood flow in the cerebral arteries, the desired gate depth is approximately 50 mm from the probe, with a bracketing gate depth range of 40 mm to 60 mm. However, other applications of the Doppler ultrasound system may dictate a different range of Doppler gate computation.

Clutter cancellation in the signal location mode outlined here is accomplished with FIR filters due to the short sequences of Doppler shift signals anticipated in order to maximize signal acquisition speed. Infinite impulse response ("IIR") filters are appropriate in the tracking mode where adjustments to the transmit and receive steering are less frequent and the sequences are significantly longer. A simple derivative filter can also be used to clutter filter the low-pass filtered data, across multiple pulse periods and at a fixed depth. For example, in a set of time series data, each pair of adjacent samples can be subtracted to produce a clutter-filtered value in the time series data. The clutter filtered Doppler shift data is then provided to the processing system 620 from each of the six TX/RX/DSP-channels 701-706. The data can be used by the processing system 620 to construct an image for display on the display 626 (FIG. 6) to provide visual feedback to an operator for the presence of blood flow in a region of interest interrogated by ultrasound at a plurality of sample locations. For example, using the Doppler shift data provided to it, the processing system 620 can construct an image of a compound mode Doppler virtual surface 116 (FIG. 2), as previously described. Although not discussed herein in detail, construction of an image from the Doppler shift data can be accomplished using conventional techniques now known by those ordinarily skilled in the art, or later developed. Consequently, in the interest of brevity, a detailed discussion of constructing such an image is omitted from herein. As will be explained in more detail below, the Doppler shift data can be further processed by the processing system 620 according to a locating algorithm to locate blood flow in a region of interest.

With the use of a locating algorithm, the DSP platform 700 and the processing system 620 can be utilized to quickly and automatically identify (i.e., locate) blood flow in a region of interest, and continue to monitor (i.e., track) the blood flow without the need for manually adjusting the location or orientation of the ultrasound probe. As will be explained in more detail below, the locating algorithm applies modern spectral estimation theory previously applied in seismic array frequency and wave number analysis for locating blood flow. More specifically, the minimum variance spectral estimation technique of Capon is applied to the collection of Doppler shift signals, each Doppler shift signal derived from a respective transducer element, for automatically locating and tracking blood flow or tissue motion.

The application of the minimum variance spectral estimation technique of Capon for the locating algorithm is described with respect to the six element transducer 400. This description will pertain to increasing detail in vicinity of one transmit direction (i.e., look direction) among all those used to tile the virtual surface 116 (FIG. 2). This discussion applies to the spatial region corresponding to the lateral extent of the transmit beam about the given look direction, and at a depth of interest. Reflections outside this region will not contribute significantly, and therefore, the corresponding "out of beam" signal processing is not performed. As previously discussed, the use of the six element transducer 400 provides a relatively simple vehicle to describe application of the algorithm. However, those ordinarily skilled in the art will obtain sufficient understanding from the description provided herein to modify the locating algorithm and tracking algorithm for application with other multi-element transducers having greater or fewer transducer elements, or having the transducer elements arranged differently.

Generally, the embodiment of the locating algorithm and tracking algorithm described herein is capable of determining locations of one fewer signal sources than the number of individual elements in the transducer. The signals here are those intersecting a spherical surface which is a constant distance, D, away from the transducer 400, such as the virtual surface 116 (FIG. 1A). In the particular application of TCD, where the signals of interest represent blood flow in the basal arteries in the brain, including the middle cerebral artery, the anterior cerebral artery, and the posterior cerebral artery, the signals are far apart relative to the transmit beam width. Therefore, there is generally one signal in the evaluation neighborhood about the given look direction. Regarding any of the basal arteries of the brain, the number of vessels in the search region and at a typical depth is one. As a result, there is very straight forward positive confirmation to perform once a signal is discovered, because generally finding more than one signal in the region of interest will be unusual.

The geometric center of each transducer element 401-406 (FIG. 4) will be referred to as the "phase center", $\vec{c}_i=(c_{xi},c_{yi})$, where i is the index of the transducer element (1 through 6). As previously discussed, the receive signals are digitized at four- or eight-times the carrier frequency, the resulting data demodulated, low-pass filtered, decimated, and clutter filtered so that baseband Doppler shift samples can be constructed for the depth D for each element and for each pulse period. After clutter filtering the samples for a fixed-gate depth, a variable $\alpha_{ij}$ is defined as the complex Doppler shift sample associated with the $i^{th}$ transducer element and the $j^{th}$ pulse period of the Doppler signal (at depth=D). For a fixed i, $\alpha_{ij}$ represents a Doppler shift signal, whereas in total, $\alpha_{ij}$ represents "Doppler shift data." The Doppler shift data collected from depth D over N pulse periods are expressed as $$P_{j=1\ldots N}=[\alpha_{1j},\alpha_{2j},\alpha_{3j},\alpha_{4j},\alpha_{5j},\alpha_{6j}]^T \quad (0.1)$$

where T denotes non-conjugated transpose. A covariance matrix of this process contains the information of interest regarding the location of blood flow or tissue motion. The covariance matrix is calculated by $$R = \text{cov}(p) = \frac{1}{N}\sum_j p_j p_j^H, \quad (0.2)$$

where H indicates conjugate transpose.

The concept of a "steering vector" will now be introduced. The steering vector is used to search across the solid angle at depth D for blood flow or tissue motion. For the purpose of providing a common frame of reference, it is assumed that the transducer is positioned in an x-y plane at a depth z=0. A plane wave moving across the transducer aimed with arbitrary spherical coordinate angles θ and φ will have phase at transducer element i expressed as $$\Phi_i = e^{j\vec{k}\cdot\vec{c}_i} = \exp\left[j\frac{2\pi}{\lambda}(c_{xi}\cos\theta\sin\varphi + c_{yi}\sin\theta\sin\varphi)\right] \quad (0.3)$$

where $\vec{c}_i=(c_{xi},c_{yi})$ is the phase center for the element and $$\vec{k} = \frac{2\pi}{\lambda}(\cos\theta,\ \sin\theta)\sin\varphi.$$

The symbol $\phi$ in these expressions represents the angle from the z-axis and runs from 0 to $\pi$, and the symbol $\theta$ represents the angle in the x-y plane, measured from the x-axis, and runs from $-\pi$ to $\pi$. A plane wave traveling in the $(\hat{\theta},\hat{\phi})$ direction will have a different phase, $\Phi_i(\theta,\phi)$, associated with each transducer element. Note that the beam direction for a steering vector is established by choosing $\theta$ and $\phi$ and calculating $\Phi_i(\theta,\phi)$ associated with each transducer element. The associated phases for all elements comprises the "steering vector":

$$s(\theta,\phi)=[\Phi_1(\theta,\phi),\Phi_2(\theta,\phi),\Phi_3(\theta,\phi),\Phi_4(\theta,\phi),\Phi_5(\theta,\phi),\Phi_6(\theta,\phi)]^T \quad (0.4)$$

The steering vector specified by the independent variables $\theta$ and $\phi$ is used to explore the signal power received from the transducer from different directions.

A minimum variance power spectrum, which indicates Doppler signal power as a function of steering direction, is expressed as a quadratic function of the steering vector and the covariance matrix inverse:

$$P^{MV}(\theta,\varphi) = \frac{1}{s^H(\theta,\varphi)R^{-1}s(\theta,\varphi)} \quad (0.5)$$

Once the region around a normal axis is explored by varying $\theta$ and $\phi$, a particular location will be identified as corresponding to the location of blood flow or tissue motion and a steering vector defined for the location, or the information from varying $\theta$ and $\phi$ will be used to fill in local flow details in the virtual surface 116 of FIG. 1B.

Apodization weights and delays to apply to the six transducer elements to steer transmit and receive signals can then be specified by the six element vector w:

$$w=R^{-1}s(\hat{\theta},\hat{\phi})P^{MV}(\hat{\theta},\hat{\phi}). \quad (0.6)$$

Here $(\hat{\theta},\hat{\phi})$ is the location of the maximum calculated Doppler signal power, $|P^{MV}|$, over the region probed with the steering vector and further probed with varying transmit direction. To electronically steer the ultrasound beam on either transmit or receive, the array apodization weight values are the magnitudes of the elements of w which are applied to each transducer element as gain coefficients, and the individual element time delays are obtained from the phases of the elements of w divided by $2\pi f_0$.

Operation of the Doppler ultrasound system 600 and the processing system 620 will now be described with specific application to TCD. As previously discussed, in locating cerebral blood flow, an acoustic window in the skull through which the blood flow can be observed by the Doppler ultrasound system is initially located. The desired blood flow is then located and monitored. A method for using the DSP platform 700 and transducer 400 to locate an acoustic window will be described below, followed by a description of a locating algorithm according to an embodiment of the invention. In addition to the DSP platform, the processing system 620 (FIG. 1) is used in executing the locating algorithm and performing the process of locating an acoustic window. It will be appreciated by those ordinarily skilled in the art, however, alternative embodiments of the invention may include additional processing sub-systems or combine some or all of the processing capabilities of the processing system 620 in the DSP platform. Thus, the scope of the invention is not limited to a particular allocation of processing between the DSP platform and the processing system 620.

Figure 10:
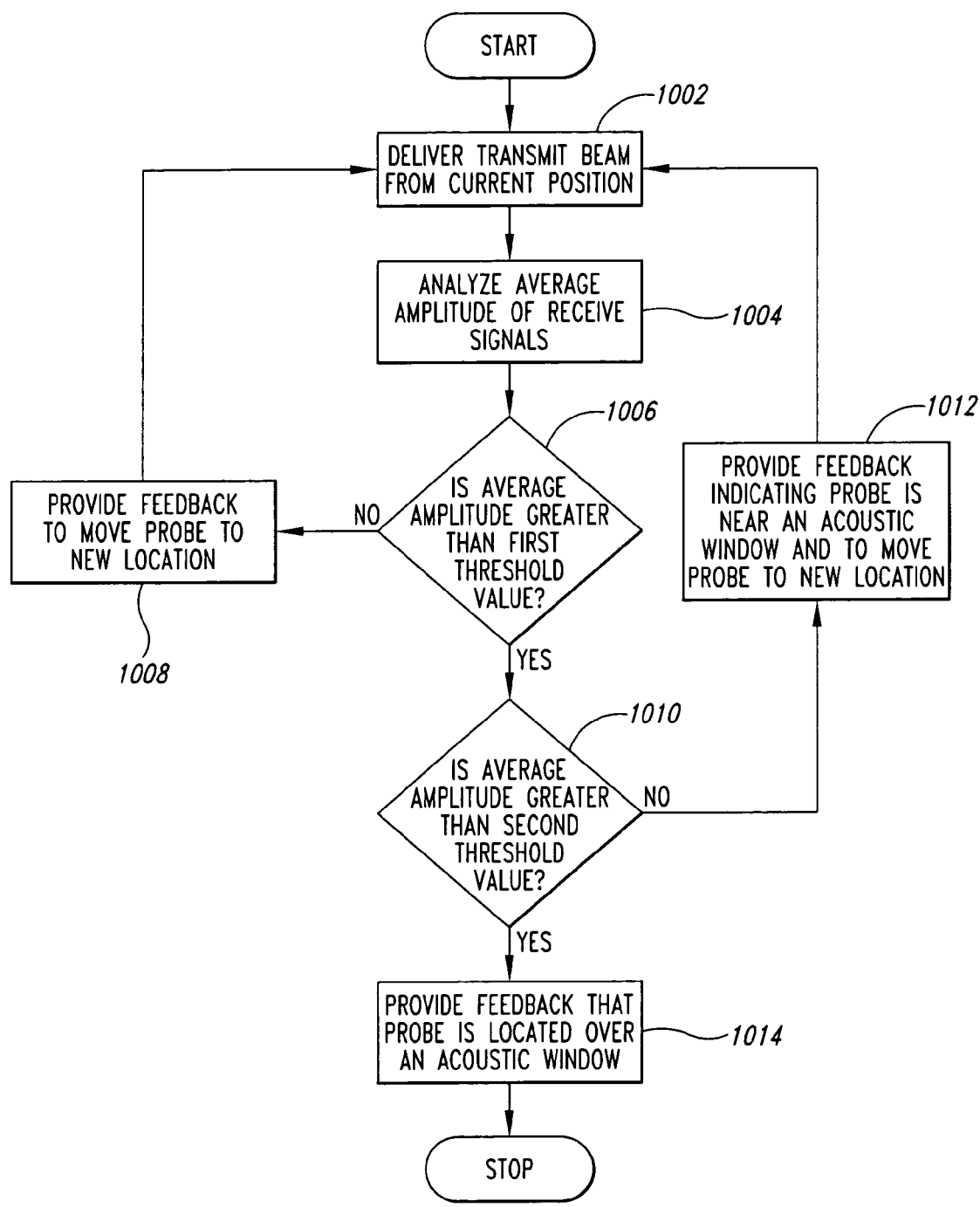
FIG. 10 is a flow diagram of a process for locating an acoustic window according to an embodiment of the invention.

FIG. 10 is a flowchart illustrating a process of identifying an acoustic window according to an embodiment of the present invention. An acoustic window is identified as a probe location from which blood flow or tissue motion can be observed using ultrasound. For example, with respect to a specific application of monitoring cerebral blood flow, the acoustic window is the location on the skull that allows one to acoustically "see" through the skull bone to observe blood flow. In finding an acoustic window, the ultrasound probe is positioned on the skull. At step 1002, transmit signals are delivered from the current position. Receive signals, resulting from reflected transmit signals, are monitored for a depth range of interest. In the specific example of locating cerebral blood flow of the middle cerebral artery, the depth range of interest is generally between 40 and 60 mm with a particular depth of interest at 50 mm. At step 1004 the amplitude of a group of receive signals are averaged and at a step 1006 are compared to a first threshold value to determine whether there is a lack of receive signals from the depth range of interest. In one embodiment, raw digital echo data can be used in generating data that is compared to the first threshold value. For example, a sum of squared amplitudes can be generated from the digitized samples with the summation starting and ending at specific depths (e.g., 40-60 mm). In another embodiment, the amplitude of each successive group of 16 ultrasound pulses are averaged. For example, an average absolute amplitude can be computed, again over a depth range, and then compared with an amplitude threshold.

If the average absolute amplitude is less than the first threshold value, it is assumed that the probe should be relocated since the reflections from the present probe location are not sufficient to indicate backscatter from underlying brain tissue, and therefore, the probe is not positioned over an acoustic window. At step 1008, the user is provided with feedback that the probe should be moved to a new location. If the average amplitude at the step 1006 is greater than the first threshold value, then at step 1010 a second threshold used to evaluate whether there is a Doppler signal somewhere in the field of view of the probe. The Doppler signal power can be calculated by summing the squared absolute values of the Doppler shift signal, and then further summed over a depth range of interest and compared to the second threshold. If the Doppler signal power is less than the second threshold, feedback is provided at stop 1012 to the user that the probe is near or over an acoustic window but there is no detected blood flow signal in the viewing range of the probe. Accordingly, the position of the probe should be changed with respect to the current location, which includes changing the direction of the probe but not the position on the skull. However, if a Doppler signal is detected, that is, the Doppler signal power is greater than the second threshold, then a second form of feedback is given to the user at step 1014 indicating that an acoustic window and underlying blood flow has been located.

In providing feedback on whether the average amplitude of the receive signals suggests the presence or absence of an acoustic window for a particular probe location, and further whether there is underlying blood flow, audio and/or visual feedback can be provided to assist the operator in finding an acoustic window. For example, audio feedback in the form of tone having a variable volume that changes as the probe is moved towards or away from an acoustic window can be used. Visual feedback in the form of an image on a graphical display can supplement or replace audio feedback. In one embodiment of the invention, a process analogous to a "stud finder" can be used. That is, the probe can be moved over the surface until a light emitting diode ("LED") emits light, indicating that the probe is over an acoustic window. The operator can then adjust probe motions to be angular ("flashlighting") rather than lateral motions across the temporal bone region, in searching for blood flow. When blood flow signals are located, a second LED may be employed to convey this information to the operator, indicating that the transducer should be secured in a fixed position over the current location. Other forms of feedback known in the art can be used as well.

After an acoustic window has been located, and the transducer is positioned accordingly, and a locating algorithm can be performed for automatically locating and tracking blood flow or tissue motion. An algorithm for automatically locating and tracking blood flow according to an embodiment of the present invention will now be described.

The algorithm has two "modes" of operation while performing the auto-location of blood flow and tracking of the same. The two modes can be generally described as a search mode, and an acquisition/track mode. In the search mode, blood flow in a region of interest is located by beam steering transmit and receive signals over a search region. An example of a search region is provided by a compound-mode Doppler virtual surface 116 having a plurality of sample locations that are interrogated with ultrasound. Based on the information obtained for the plurality of sample locations, blood flow is located. In acquisition/track mode, the located blood flow is acquired and processed. A set of apodization weights and delays, represented by a steering vector, are applied to the individual elements of a multi-element transducer, such as the transducer 400, in locating, acquiring and tracking the acoustic reflector of interest. The set of weights and delays determines the form and direction of the ultrasound that is delivered by the transducer. Steering vectors which accomplish electronic beam steering across two degrees of angular freedom are both utilized and derived in search mode to determine where blood flow is located. Steering vectors may also be utilized in different fashion. A general "raster scan" search may be employed to search in a brute force fashion for blood flow in a region of interest. A second type of search may employ signal processing search algorithms such as a gradient search or a simplex search, and more quickly accomplish target location. These latter techniques may be employed with broader beam shapes, that is, beams that are significantly larger than the target and having substantial size regarding the search region. These sorts of beams will be more amenable to giving steering feedback when the maximum intensity portion of the beam is pointed away from the target, but the target still rests inside the mainlobe of the beam. A broader beam may be formed by apodization (both amplitude and phase) of the transducer elements, as known in the art.

The steering vector identifying blood flow in the region of interest is then carried into the acquisition/track mode of operation. The locating algorithm generally uses a fixed steering vector in acquisition/track mode. Updates are made to the steering vector in acquisition/track mode based on incidental changes in the location of the blood flow relative to the probe, which may be instigated by a variety of phenomena. For example, the changes can be caused by the patient moving his head and the probe being blocked from following this motion, the probe being jarred into a new position by a surgeon's elbow, and pronounced mastication. Changes in the location of blood flow can be sensed by continually evaluating the local neighborhood of the transmit beam look direction associated with the acoustic reflector of interest, or intermittently scanning a broader region about the transmit beam look direction associated with the location of blood flow. In either method, an updated look direction is established for the acoustic reflector of interest.

In alternative embodiments of the invention, the spacing and number of sample locations interrogated in the region of interest can be modified according to the mode of operation of the locating algorithm. That is, during search mode, to survey a large region of interest, the number of sample locations and the spacing of the sample locations can be selected to interrogate a large region of interest. When blood flow is acquired from executing the locating algorithm, and the ultrasound is steered in the direction of the location of the blood flow, the number of sample locations and/or the spacing of the sample locations in the region surrounding the location identified for the blood flow can be changed from the number and spacing of the sample locations used during search mode. In this manner, modifying the number and spacing of the sample locations from one mode to another can be advantageously used to efficiently search a region in search mode, and then used to obtain high resolution information from a region adjacent the located acoustic reflector of interest. More generally, changing the number of sample locations, as well as the spacing or density of sample locations is a modification that can be made without departing from the scope of the present invention.

As previously discussed, blood flow at a depth of interest in a region of interest is initially located during the search mode. In the search mode, the ultrasound transmit and receive signals are steered to a plurality of look directions over a search region, and information is acquired for a depth range bracketing the depth of interest for each corresponding sample location. In one embodiment, the sample locations correspond to a respective look direction across a compound-mode Doppler virtual surface 116, as previously discussed with respect to FIG. 2. Information at several different depths in the depth range can be taken for each look direction. The depth range bracketing the depth of interest can span approximately 20 mm and include between five and 10 different depths. Data is acquired from each depth. As will be explained in more detail below, the information acquired at the different depths will be used to confirm that a potential blood flow signal is not an artifact or spurious noise. The locations and the depth range for which information is acquired can be preset to provide a scanning pattern that facilitates locating blood flow. Various factors can be considered and balanced in establishing a scanning pattern. For example, the size of the search region, the number of sample locations at which information is acquired, the desired resolution to locate blood flow in the search region. Additionally the number of sample locations should be balanced against the processing overhead of the DSP platform 700 and the processing system 620 in which the locating algorithm is executed.

For each of the look directions and for the different depths in the depth range bracketing the depth of interest at which information is acquired, the Doppler signal strength of the receive signal from the respective location and depth is calculated. Conventional algorithms can be used for the calculation of the Doppler signal strength for the different locations and the different depths. Previous discussions describing the calculation of Doppler signal power can also be applied. An example of a suitable process for calculating Doppler signal strength is described in the aforementioned U.S. Pat. No. 6,196,972 to Moehring, which has been incorporated herein by reference. The power values calculated for the different locations and depths form an array of data from which a location corresponding to a maximum calculated power for a depth of interest can be determined. The identified location represents the location of blood flow in the region of interest. A steering vector corresponding to the direction of the identified location is calculated and a set of apodization weights and delays are resolved for electronically beam steering transmit and receive signals in the direction of the blood flow.

The location of blood flow can be confirmed by comparing the calculated Doppler signal strength for the location at the depth of interest with the calculated Doppler signal strength in the same look direction for at least one other depth in the depth range. Confirmation is made if the calculated Doppler signal strength for the same look direction but at the different depth or depths is a value that is consistent with a blood flow signal that is present at multiple depths. In contrast, if the calculated Doppler signal strength for the same look direction and different depth indicates that a sufficient Doppler signal strength is present only for the depth of interest, it is unlikely that the location corresponds to blood flow in the region of interest.

After a location for the blood flow is identified in the search mode, the ultrasound system enters an acquisition/track mode during which the steering vector identifying the location of the blood flow at the depth of interest is updated by applying the minimum variance spectral estimation technique previously described. A new location corresponding to the peak of the minimum variance power spectrum provides the updated direction for electronically beam steering the transmit and receive signals. Specifically, the updated steering vector is determined by calculating a power spectrum for a region proximate to the "old" location of the acoustic reflector of interest by varying the direction of the old steering vector. As previously discussed, the direction of the steering vector can be defined by two spherical coordinate angles, $\theta$ and $\phi$, relative to the transducer. The $\theta$ and $\phi$ corresponding to the maximum calculated power over the region proximate the old location is used to identify the updated steering vector defining an updated location of blood flow. Based on the updated steering vector that is calculated, the appropriate apodization weights and delays are resolved and applied to steer the transmit and receive signals in the direction of the updated location. With the updated location of blood flow identified and the apodization weights and delays determined, the transmit and receive signals are electronically steered to monitor the blood flow by acquiring and processing data from the updated location.

The minimum variance power spectrum can be calculated concurrently with the monitoring activity, which minimizes any discontinuities in the information that may occur in updating the transmit and receive beamformers with the new direction. It will be appreciated that the update will result in a discontinuity in the Doppler shift signal, and therefore, cannot be updated continually due to spectral analysis artifacts. As a result, updating can be performed every one or two seconds instead, or alternatively, whenever a new location is greater than a threshold distance from the old location.

In the event the position of the probe has shifted to such a degree that the blood flow signals are no longer in the region proximate to the current steering vector, the search mode is reentered to again locate the blood flow. In one embodiment, the maximum calculated power of the power spectrum is compared to a minimum threshold value to determine if this occurs. The minimum threshold value should be selected such that a calculated maximum power value below the threshold value is a good indication that the probe position has shifted enough so that the transmit and receive signals are no longer aimed in the general direction of the location of blood flow. If the maximum calculated power is below the minimum threshold, then it can be assumed that the blood flow is no longer within the search region probed by adjusting the $\theta$ and $\phi$ of the current steering vector. In response, the search mode is reentered and the process of locating blood flow, followed by acquisition and processing of data from the direction of the located blood flow, is performed as previously described.

Figure 11:
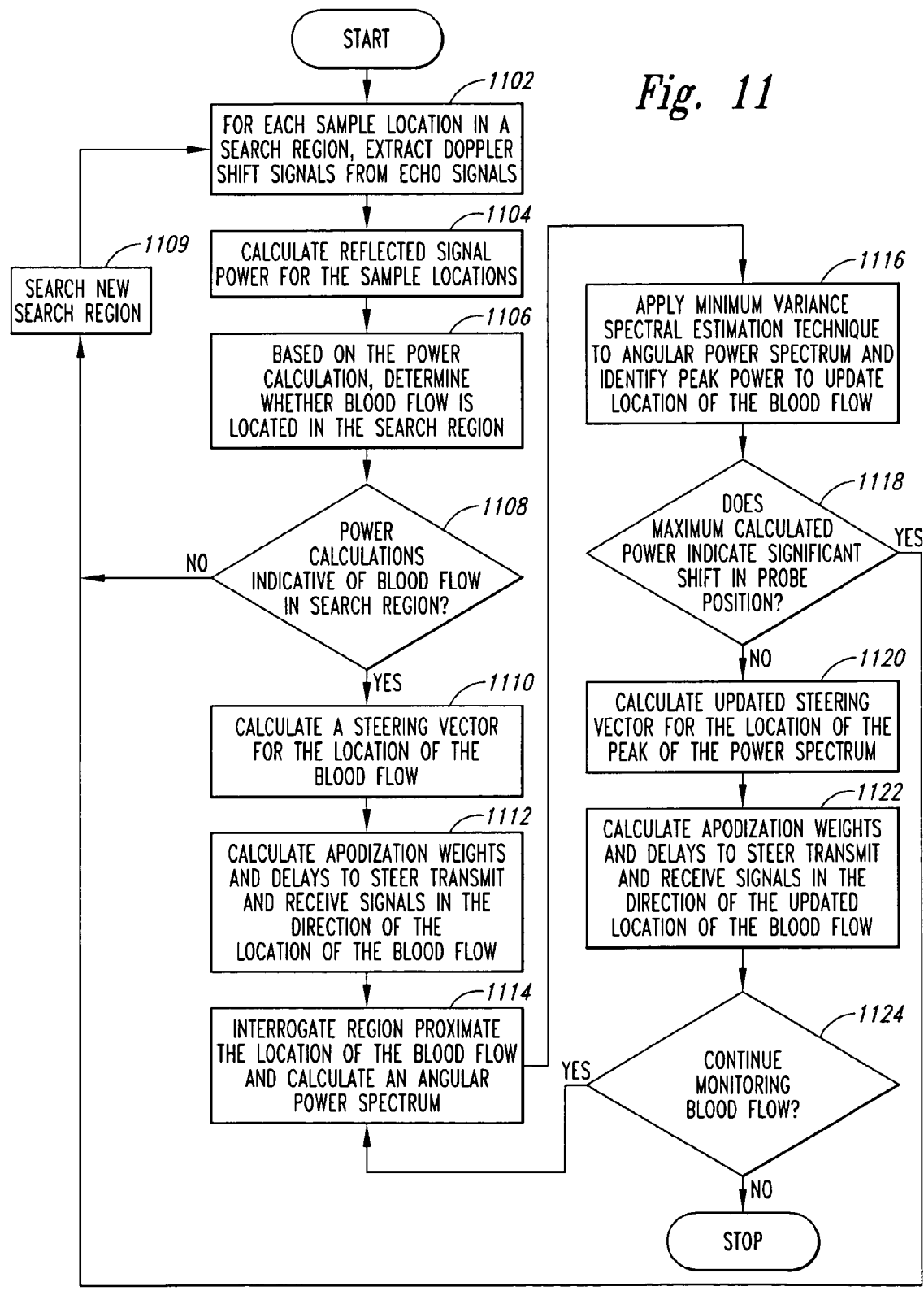
FIG. 11 is a flow diagram of a process for locating blood flow of interest according to an embodiment of the invention.

In summary, after positioning a probe having the multi-element transducer, such as the transducer 400, over an acoustic window, the previously described algorithm can be utilized to quickly and automatically locate blood flow in a search region and continue to monitor the blood flow. FIG. 11 is a flow diagram illustrating the general process of the locating algorithm according to an embodiment of the present invention. At step 1102, for each sample location sampled, Doppler shift signals are extracted from the echo signals. An example of extracting Doppler shift signals was previously described. At step 1104, Doppler signal strength for the sample locations is calculated. Based on the Doppler signal strength calculation at step 1104, it is determined whether an acoustic reflector of interest is located in the search region at step 1106. At step 1108, if the power calculation does not indicate blood flow in the current search region, the ultrasound probe is repositioned and a new search region is interrogated at step 1109. The process returns to step 1102 to begin extracting Doppler shift signals from the echo signals of the new search region. If, however, blood flow is identified at step 1108, a steering vector is calculated for the location of the blood flow at step 1110. Using the steering vector, apodization weights and delays are calculated to electronically steer transmit and receive signals in the direction of the location of blood flow at step 1112. Following step 1112, the blood flow has been acquired and can be monitored.

Tracking of the blood flow generally begins at step 1114, where a region proximate to the location of the blood flow is interrogated with ultrasound and an angular power spectrum is calculated for the interrogated region. At step 1116 a minimum variance spectral estimation technique is applied to the angular power spectrum to identify a location of peak power corresponding to an updated location for the blood flow. At step 1118, if the maximum calculated power from step 1116 is no longer indicative of blood flow located in the proximate region interrogated at step 1114, suggesting that the probe has significantly shifted and the blood flow will need to be reacquired, a search mode is reentered through step 1109 to perform a search of a search region that is broader than the region interrogated at step 1114.

However, if at step 1118 the maximum calculated power does indicate that blood flow is in the region interrogated, and the updated location of the blood flow is sufficiently distant from the former location of the blood flow, an updated steering vector for the updated location of the blood flow (corresponding to the location of peak calculated power) is calculated at step 1120. At step 1122, apodization weights and delays are calculated to electronically steer transmit and receive signals in the direction of the updated location of the blood flow. At step 1124, if the monitoring of the blood flow is to continue, the tracking process begins again by returning to step 1114. Otherwise, the tracking process terminates.

As previously discussed, in the specific application of observing blood flow in the vicinity of the proximal MCA, although embodiments of the present invention directed to the specific application are not limited to such, it is preferable for a virtual surface 116 (FIG. 2) to have a diameter of 20 mm or greater. As also previously mentioned, beam steerability and beam width are factors that respectively affect the diameter of the virtual surface 116 and the number of look directions used to tile the area with sufficient density for locating blood flow in the search region. These factors are in turn determined by element size, gross array dimensions, and apodization. For example, as known in the art, generally, the larger the element size, the lower the steerability. Additionally, the larger the gross array aperture dimensions, the narrower the resulting beam. As a result, delivering ultrasound having a relatively narrow beam may dictate including space between adjacent elements (given a limited number of elements to utilize), which in turn raises the issue of "grating lobes." Moreover, in deciding the arrangement and number of transducer elements to include in a multi-element transducer array, some practical considerations should be made. For example, the number of transducer elements may be limited by the complexity and the cost of the associated electronics associated with operating such an ultrasound transducer. Thus, as demonstrated by the specific example, in designing a multi-transducer array for a specific application, several factors, such as the number and arrangement of transducer element, should be considered.

Figure 12:
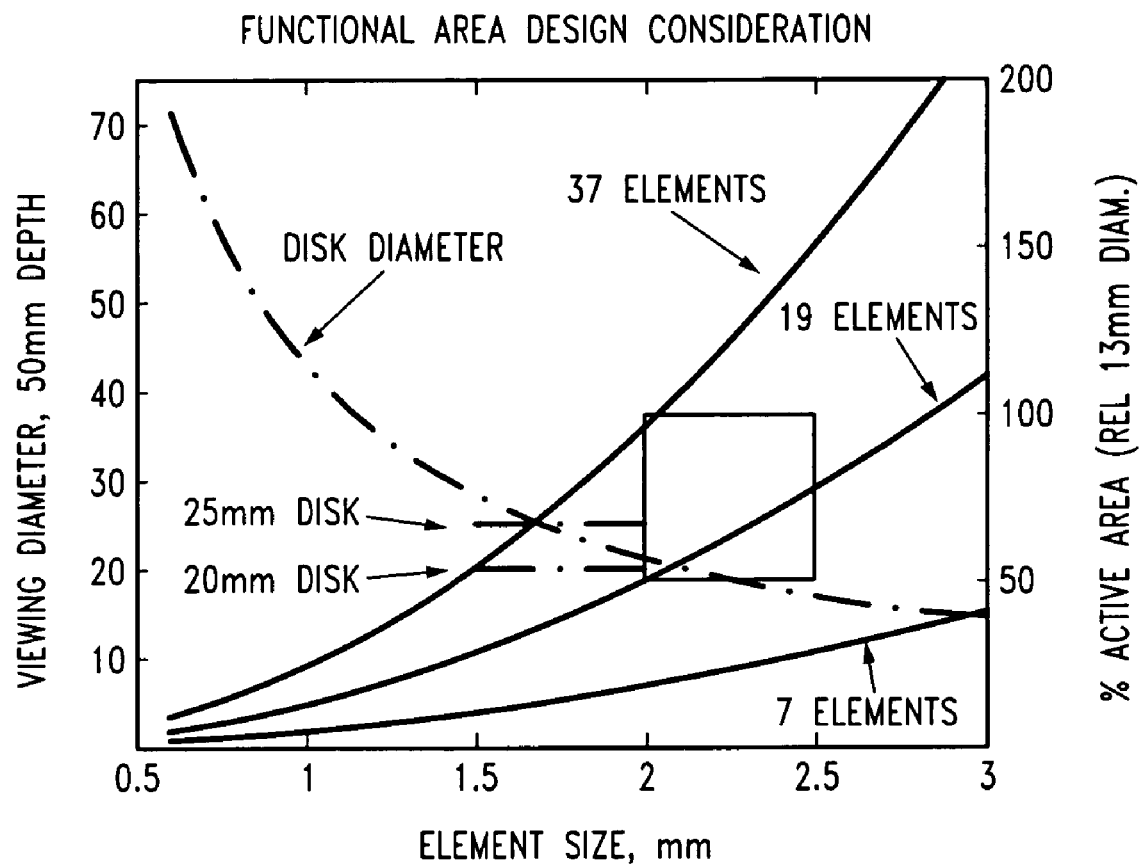
FIG. 12 is a diagram showing relationships between various ultrasound transducer parameters.

FIG. 12 illustrates various relationships between beam steering capability, number of elements, and transducer element size, as related to total active area of a 13 mm diameter probe surface delivering 2 MHz pulsed ultrasound. The beam steering capability is represented by the "viewing diameter" of a virtual surface 116 for a depth of 50 mm from the probe surface. As shown in FIG. 5, a suitable element size for the application of monitoring blood flow of the MCA, that is, at a depth of 50 mm and a virtual surface of 20 to 25 mm in diameter, is between 2.0 and 2.5 mm to provide sufficient beam steering. As previously mentioned in order to maintain "entrance beam dimensions" at the skull corresponding to a safe and reasonable heating level of the temporal bone (thermal index cranial, TIC<2), an ultrasound probe having a diameter of 13 mm is selected. The probe size results in a specific inter-element spacing for a given number of elements, which also results in "dead space" between elements. The dead space effectively moderates the active area of the probe. The right-hand axis of FIG. 12 shows the percentage active area and the three curves correspond to different numbers of active transducer elements used for generating the ultrasound beam. More specifically, the three curves correspond to delivering ultrasound from 7, 19 and 37 active elements.

Based on the criteria previously described for the application of monitoring blood flow of the MCA, FIG. 12 suggests that a 19 element probe is preferable. The resulting 19 element probe has about 60% active area compared to a solid piston having a 13 mm diameter. Although the 19 elements compose only 60% of the 13 mm diameter, the voltage applied to this probe can be increased to moderate the effect of delivering ultrasound from a reduced active area.

Figure 13A:
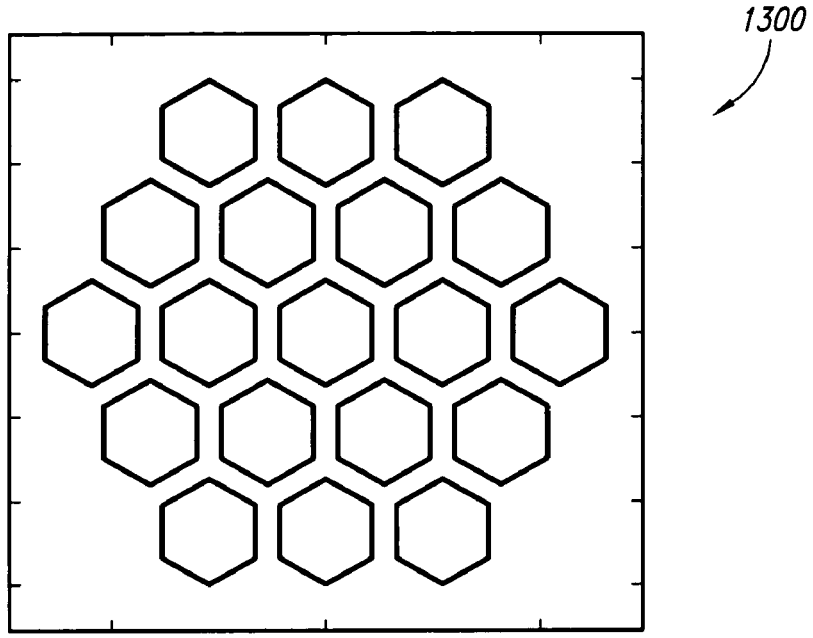
FIGS. 13A-13C are plan drawings of multi-element transducers according to embodiments of the invention.
Figure 13B:
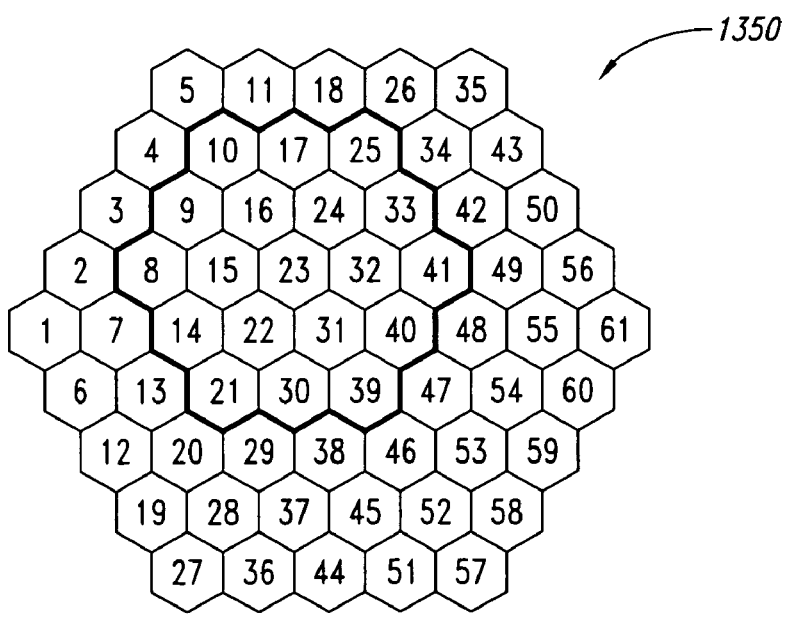
Figure 13C:
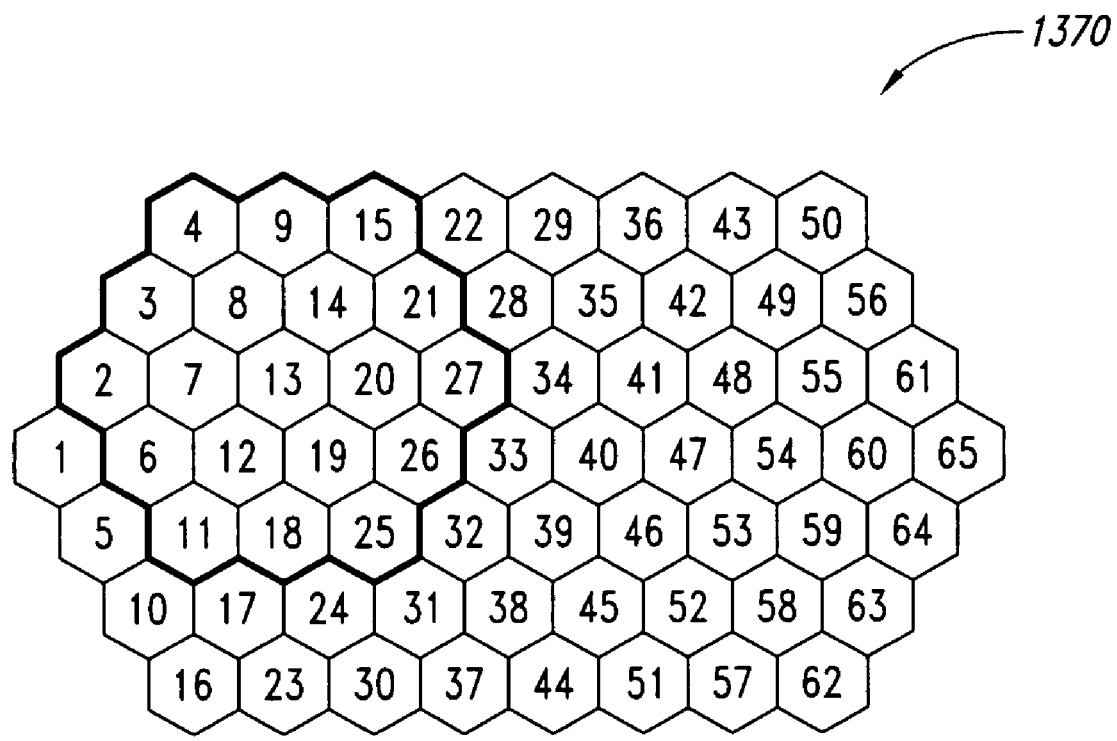

FIGS. 13A-13C illustrate multi-element transducers 1300, 1350, and 1370 according to alternative embodiments of the present invention. The multi-element transducers 1300, 1350, and 1370 are examples of multi-element transducers that are designed considering factors previously discussed with reference to FIG. 12. The individual elements of the transducers are foreseen to have lower side lobe activity and greater circular symmetry when compared to the triangular elements of FIG. 5B. Additionally, the individual elements are smaller, and as a result, will broadcast a spatially wider beam (+i−10 mm laterally at 50 mm depth) in comparison to the elements of the transducer 400. This enables a greater degree of beam steering. However, a trade off with using a greater number of smaller elements is the cost of controlling them, which can be costly both in design efforts and in resulting instrumentation size, and decreased power output from any given element.

The transducers 1300, 1350, and 1370 have 19 active transducer elements. In the transducer 1300, the 19 elements are configured as shown in FIG. 10A, and are used without any additional transducer elements. In contrast, the transducers 1350 and 1370 have an array of transducer elements, and 19 transducer elements of the transducers 1350 and 1370 are used for an "active" transducer area. The 19 element footprint may be shifted around the total footprint of the transducers 1350 and 1370 during the process of locating and tracking signals of interest.

The transducers 1300, 1350, and 1370 use the same basic elemental tile, which is a hexagon with 2 to 2.5 mm distance between sides (not vertices). The ultrasound transducers 1300, 1350, and 1370 preferably have each transducer element tuned to 50 ohms, a cable that will not exceed about 5 mm diameter, quarter wave matching layer, 2 MHz carrier frequency, minimum 20 percent bandwidth, cross talk not to exceed −30 dB between adjacent elements, electrical cross talk to be 5 to 10 dB lower than mechanical cross talk, a 200 micron kerf, and a Faraday shield around the entire probe which includes the cabling back to chassis.

The transducers 1300, 1350, 1370 designed with the idea of minimizing operator requirements for moving the probe around the temporal bone region while the system samples for underlying blood flow in TCD applications. The transducer 1370 can be placed with its longitudinal axis parallel to a line drawn between the ear and the eye, and then moved around the temporal bone region. A local transducer group of 19 active transducer elements are shown in bold lines in FIGS. 10B and 10C. It will be appreciated that if the local transducer group is translated the width of one element to the right, certain new elements will become part of the active transducer area and others will no longer be part of the active transducer area. There are some advantages to having the local transducer footprint as small as the outlined 19 element regions in FIGS. 10B and 10C, or even smaller. For example, the smaller transducer footprint provides a broader transmitted beam, and will result in fewer "interrogations"—outgoing pulses—for a search region. However, a necessary consideration of the size of the local transducer footprint is the possible increase in thermal index cranial.

The transducers 1300, 1350, and 1370 can be utilized with a DSP platform that is capable of driving at least 19 transducer elements independently, and to receive and process receive signals detected by at least 19 transducers. Although the DSP platform 700 of FIG. 7 was described as including only 6 independently controlled TX/RX/DSP channels 701-706, those ordinarily skilled in the art will obtain sufficient understanding from the description provided herein to provide a DSP platform that can be used with the transducers 1300, 1350, and 1370. Such modifications remain within the scope of the present invention.

Although FIG. 12 suggests using 19 active transducer elements is preferable for the specific application of monitoring blood flow in the MCA, and transducers 1300, 1350, and 1370 are shown having 19 active transducer elements, the number of active transducers, the elemental tile shown, and the arrangement and number of transducer elements in an array, have been provided by way of example. The previous description is directed to particular embodiments of the invention, and are not intended to describe limitations limiting the scope of the present invention.

Turning to an alternative embodiment of the invention, the functionality previously described are combined to provide automatic detection and tracking of blood flow with assessment of characteristics of the blood flow. FIGS. 14A-14D illustrate various images that are displayed to an operator during operation of an embodiment of the present invention that provides the combined functionality. Some or all of the principles previously described can be applied in the present embodiment of the invention. As previously discussed, those ordinarily skilled in the art will obtain sufficient understanding of the invention from the description provided herein to practice the invention, including the present alternative embodiment.

Figure 14A:
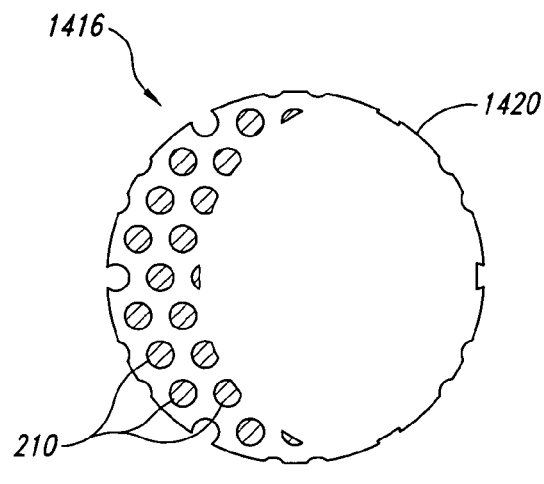
FIGS. 14A-14D are diagrams of visual feedback provided to an operator in accordance with an embodiment of the invention during a process of locating blood flow in a region of interest and evaluating the blood flow.

FIG. 14A illustrates an image of a virtual surface 1416 for a first position of an ultrasound probe on a patient's skull. As previously described with respect to the virtual surface 116 (FIG. 2), a plurality of sample locations are interrogated, and information obtained from each of the sample locations can be used to construct the virtual surface 1416. The image has a shadow region 1420 on the right hand side of the image of the virtual surface 1416. The portion of the virtual surface 1416 corresponding to the shadow region 1420 represents the region ultrasound cannot penetrate bone of the skull, that is, a region not aligned with an acoustic window. In contrast, the left side of the image of the virtual surface 116 is partially covered with gray signals for the look directions 210. The gray coloration indicates that the ultrasound can penetrate the bone for the corresponding look directions 210, but that the reflections being observed for the depth of interest do not contain Doppler information indicating blood flow. The information for constructing the image of the virtual surface 1416 can be obtained through the acoustic window locating algorithm previously described, as well as the construction of Doppler shift information for the plurality of sample locations in the region of interest, represented in FIG. 14A as a compound mode Doppler virtual surface 1416.

Figure 14B:
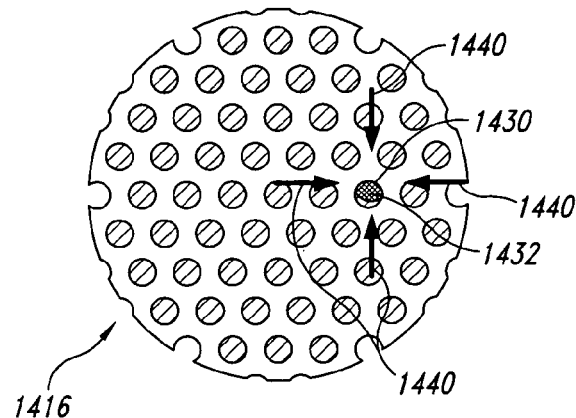
Figure 14C:
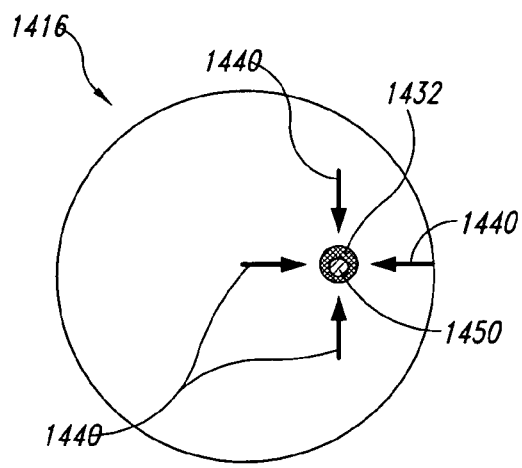
Figure 14D:
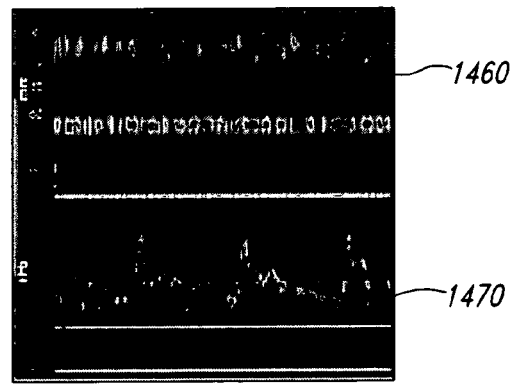

FIG. 14B illustrates an image of the virtual surface 1416 for a second position of the ultrasound probe on the patient's skull. An acoustic window locating algorithm providing sufficient information to construct the visual feedback image enables an operator to move the probe from the first location illustrated in FIG. 14A to an acceptable location over an acoustic window, as shown in FIG. 14B. In contrast to FIG. 14A, the image of the virtual surface 1416 of FIG. 4B does not have any shadow regions 1420, indicating that all of the look directions 210 across the virtual surface 1416 are aimed through an acoustic window. A locating algorithm is executed to process the data obtained for the plurality of sample locations in order to locate blood flow, as previously described. Additionally, using the Doppler shift signals extracted from the echo signals from each of the sample locations, blood flow information can be generated. A red signal (not shown in color in FIG. 14B) is displayed for a look direction 1430. The red signal represents a Doppler blood flow signal 1432 automatically detected for the look direction 1430 and at the depth of interest. The blood flow signal 1432 will remain displayed as long as blood flow is detected for the look direction 1430 and the probe remains in the same position. The blood flow signal 1432 can be further visually highlighted to alert the operator that a flow signal has been detected. As shown in FIG. 14B, the blood flow signal 1432 in the look direction 1430 is highlighted by a set of arrows 1440 pointing to the signal 1432. The highlighting indicates that blood flow has been identified using the locating algorithm, which is typically associated with a search mode, as previously described. The image of the virtual surface 1416 in FIG. 14B can be simplified to show an outline of the virtual surface 1416 and the detected blood flow signal 1432, as illustrated in FIG. 14C. The image, while not displaying any of the look directions 210, focuses the operator on the detected blood flow signal 1432. The image of FIG. 14C is provided after the acquisition/track mode has been entered. That is, after interrogating the region of interest by surveying a plurality of sample locations (i.e., search), blood flow in the search region has been identified (i.e., acquisition). A circle 1450 within the blood flow signal 1432 is highlighted and represents the blood flow signal being tracked by the system. The image of FIG. 14C can be switched to the image of FIG. 14D, which illustrates a PMD image 1460 and a spectrogram image 1470 at the depth of interest for the blood flow signal being tracked. As previously discussed, the PMD image 1460 can be used to display blood flow information in a time domain for the depth of interest.

As illustrated in the present example, the functionality of locating an acoustic window, automatically detecting blood flow, automatically tracking blood flow, and further providing a PMD/spectrogram image of the blood flow can be combined to provide a tool for easily detecting and locating blood flow information, and monitoring the same for application in TCD.

From the foregoing it will be appreciated that, although specific embodiments of the invention have been described herein for purposes of illustration, various modifications may be made without deviating from the spirit and scope of the invention. For example, the compound-mode Doppler virtual surface previously discussed can be constructed by electronically steering an ultrasound beam to interrogate a plurality of sample locations in a region of interest. In one modification, the entire compound-mode Doppler virtual surface can be swept or scanned over a larger region. That is, generally, a compound-mode Doppler virtual surface is constructed while the probe is pointed and positioned at a first location. As the probe orientation or location is moved, the virtual surface will be constructed for the region at which the probe is now aimed. Thus, the entire virtual surface can be swept to cover a larger region of interest. Accordingly, the invention is not limited except as by the appended claims.

What is claimed is:

1. A processing system for a Doppler ultrasound system having a transmit circuit configured to independently drive transducer elements of a multi-element transducer to deliver ultrasound to different positions relative to a normal axis extending from the multi-element transducer and further having a receive circuit configured to generate respective receive echo signals resulting from the ultrasound delivered to the different positions in response to each of the transducer elements detecting echo signals, the processing system comprising:

an analog-to-digital converter (ADC) circuit operably coupled to the receive circuit and configured to digitize the receive echo signals into data representing the respective receive echo signals;
a memory for storing data; and
a processor operably coupled to the ADC and transmit circuit and configured to generate control signals to control the transmit circuit to steer ultrasound beams from the transducer and along respective beam axes to respective sample locations, the sample locations arranged spatially across a virtual surface having a lateral extent, wherein each beam axis intersects the virtual surface at only the respective sample location, the processor further configured to process the data from the receive circuit to extract Doppler shift signals and generate Doppler shift data therefrom for each of the sample locations, and configured to store the Doppler shift data for the sample locations in the memory.

2. The ultrasound system of claim 1 wherein the processor is configured to process the data from the receive circuit to extract Doppler shift signals and generate the Doppler shift data by:
bandpass filtering the echo signals at a first frequency;
digitizing the filtered echo signals into digital data representing the filtered echo signals;
processing the digital data to provide data representing demodulated filtered echo signals;
digitally low-pass filtering the data representing the demodulated filtered echo signals; and
decimating the digitally low-pass filtered data over a depth to the depth of interest to provide Doppler shift data.

3. The ultrasound system of claim 1 wherein the processor is further configured to process the Doppler shift data to calculate a power for the Doppler signals for the sample locations.

4. The ultrasound system of claim 1 wherein the processor is further configured to process the Doppler shift data to determine a direction of motion for detected motion at the sample locations.

5. The ultrasound system of claim 1 wherein the processor is further configured to process the Doppler shift data to calculate a power for the Doppler signals for the sample locations and determine a direction of motion for detected motion at the sample locations.

6. The ultrasound system of claim 5 wherein the processor is further configured to generate data for displaying the calculated a power for the Doppler signals for the sample locations and the direction of motion for the detected motion at the sample locations.

7. The ultrasound system of claim 1 wherein the ADC circuit comprises a plurality of ADC circuits, each ADC circuit configured to digitize a respective receive echo signal from the receive circuit.

8. A processing system for a Doppler ultrasound system having a transmit circuit configured to independently drive transducer elements of a multi-element transducer to deliver ultrasound to different positions relative to a normal axis extending from the multi-element transducer and further having a receive circuit configured to generate respective receive echo signals resulting from the ultrasound delivered to the different positions in response to each of the transducer elements detecting echo signals, the processing system comprising:
an analog-to-digital converter (ADC) circuit operably coupled to the receive circuit and configured to digitize the receive echo signals into data representing the respective receive echo signals; and
a processor operably coupled to the ADC and transmit circuit and configured to generate control signals to control the transmit circuit to deliver ultrasound to a plurality of sample locations arranged spatially across a region of interest, wherein the sample locations construct a surface including a region having lateral extent and each sample location of the region having a respective beam axis, the processor further configured to process the data from the receive circuit to extract Doppler shift signals and calculate a power for the Doppler signals for the sampling locations.

9. The ultrasound system of claim 8 wherein the processor is further configured to process the Doppler shift data to calculate power for the Doppler signals for the sampling locations to determine a location of blood flow.

10. The ultrasound system of claim 8 wherein the processor is further configured to process the Doppler shift data to determine a direction of motion for detected blood flow at the sample locations.

11. The ultrasound system of claim 8 wherein the processor is configured to process the data from the receive circuit to extract Doppler shift signals and generate the Doppler shift data by:
bandpass filtering the echo signals at a first frequency;
digitizing the filtered echo signals into digital data representing the filtered echo signals;
processing the digital data to provide data representing demodulated filtered echo signals;
digitally low-pass filtering the data representing the demodulated filtered echo signals; and
decimating the digitally low-pass filtered data over a depth to the depth of interest to provide Doppler shift data.

12. The ultrasound system of claim 1 wherein the virtual surface constructed from the plurality of sample locations is planar.

13. The ultrasound system of claim 8 wherein the surface constructed from the plurality of sample locations is planar.

* * * * *